(12) United States Patent
Gonzalez et al.

(10) Patent No.: US 9,345,710 B2
(45) Date of Patent: May 24, 2016

(54) INHIBITORS OF PHOSPHATIDIC ACID PHOSPHOHYDROLASE (PAP) ENZYMES FOR THE TREATMENT OF CANCERS THAT DEPEND ON MEMBERS OF THE ERBB/HER TYROSINE KINASE RECEPTOR FAMILY

(75) Inventors: Alfonso Gonzalez, Santiago (CL); Andrea Soza, Santiago (CL); Claudia Metz, Santiago (CL)

(73) Assignee: PONTIFICA UNIVERSIDAD CATOLICA DE CHILE, Santiago (CH)

( * ) Notice: Subject to any disclaimer, the term of this patent is extended or adjusted under 35 U.S.C. 154(b) by 38 days.

(21) Appl. No.: 13/984,012

(22) PCT Filed: Feb. 6, 2012

(86) PCT No.: PCT/CL2012/000005
§ 371 (c)(1),
(2), (4) Date: Feb. 5, 2014

(87) PCT Pub. No.: WO2012/135970
PCT Pub. Date: Oct. 11, 2012

(65) Prior Publication Data
US 2014/0142087 A1 May 22, 2014

(30) Foreign Application Priority Data

Feb. 8, 2011 (CL) .................................. 273-2011

(51) Int. Cl.
| | | |
|---|---|---|
| *A61K 31/138* | (2006.01) | |
| *A61K 31/55* | (2006.01) | |
| *A61K 31/133* | (2006.01) | |
| *A61K 31/366* | (2006.01) | |
| *A61K 31/5415* | (2006.01) | |
| *A61K 45/06* | (2006.01) | |

(52) U.S. Cl.
CPC .............. *A61K 31/55* (2013.01); *A61K 31/133* (2013.01); *A61K 31/138* (2013.01); *A61K 31/366* (2013.01); *A61K 31/5415* (2013.01); *A61K 45/06* (2013.01)

(58) Field of Classification Search
CPC ............................ A61K 31/55; A61K 31/138
See application file for complete search history.

(56) References Cited

U.S. PATENT DOCUMENTS

2006/0009506 A1* 1/2006 Westwick et al. ............. 514/395

FOREIGN PATENT DOCUMENTS

| WO | WO 2009/070609 A2 | 6/2009 |
| WO | WO 2009/111648 A1 | 9/2009 |
| WO | WO 2012/030234 A1 | 3/2012 |

OTHER PUBLICATIONS

Sebastian et al. Biochemica et Biophysica Acta 1766, 2006, pp. 120-139.*
Powe et al. Oncotarget, Oct. 19, 2010, vol. 1, No. 7, pp. 628-638.*
Schuller. Ocnotarget, Nov. 11, 2010, vol. 1, No. 7, pp. 466-469.*
Liao X et al: 2010, "Effects of propranolol in combination with radiation on apoptosis and survival of gastric cancer cells in vitro", *Radiation Oncology*: 5: 98.
Sun B et al: 2008, "Inhibition of $Ca^{2+}$ - Independent Phospholipase $A_2$ Decreases Prostate Cancer Cell Growth by p53-Dependent and Independent Mechanisms", *The Journal of Pharmacology and Experimental Therapeutics*: 326: 59-68.
Chang H et al: 2008, "Desipramine-induced apoptosis in human PC3 prostate cancer cells: Activation of JNK kinase and caspase-3 pathways and a protective role of [$Ca^{2+}$], elevation", *Toxicology*: 250: 9-14.
Huang C et al: 2007, "Desipramine-induced $Ca^{2+}$ movement and cytotoxicity in PC3 human prostate cancer cells", *Toxicology in Vitro*: 21: 449-456.
Kabolizadeh P et al: 2011, "Platinum anticancer agents and antidepressants: desipramine enhances platinum-based cytotoxicity in human colon cancer cells", *JBIC Journal of Biological Inorganic Chemistry*: 17: 123-132.

* cited by examiner

*Primary Examiner* — James D Anderson
(74) *Attorney, Agent, or Firm* — Knobbe Martens Olson & Bear LLP

(57) ABSTRACT

Compounds and combinations of them that inhibit phosphatidic phosphohydrolase (PAP) enzymatic activity are formulated into pharmaceuticals useful in cancer treatment. Inhibitors of PAP can be used for blocking the progression of cancers that depend on the epidermal growth factor receptor (EGFR), its oncogenic variants and other members of its ErbB tyrosine kinase receptor family, through induction of their endocytosis, thus making them inaccessible to the extracellular stimuli that promote maintenance and progression of cancer.

6 Claims, 7 Drawing Sheets

INHIBITORS OF PHOSPHATIDIC ACID PHOSPHOHYDROLASE (PAP) ENZYMES FOR THE TREATMENT OF CANCERS THAT DEPEND ON MEMBERS OF THE ERBB/HER TYROSINE KINASE RECEPTOR FAMILY

CROSS-REFERENCE TO RELATED APPLICATIONS

This application is the U.S. National Phase under 35 U.S.C. §371 of International Application PCT/CL2012/000005, filed Feb. 6, 2012, which was published in a non-English language, which claims priority to CL Patent Application no. 0273-2011, filed Feb. 8, 2011.

FIELD OF THE INVENTION

The present invention describes the use of inhibitors of fosfatidic acid phosphodydrolase (PAP) enzymes (Lipins1-3 and LPP1-3) (1), either as single compounds or as combinations of them, for the formulation of medicines useful for cancer treatments.

BACKGROUND OF THE INVENTION

Cancer as a Health Problem

Cancer encompasses a group of diseases generated by uncontrolled and invasive growth of abnormal cells, which without effective treatment can result in patient's death within short periods of time (<12 months or even in 5-9 months in the most malignant cases). These number will increase in the future due to population growth, higher live expectations leading to aging, and higher exposure to risk factors. An estimation considers that new cases can increase 50% in the next 20 years, reaching 15 millions towards the year 2020. In industrialized countries 1:4 persons will die of cancer (65) (66). Thus, by frequency and mortality rate, cancer constitutes a serious problem of public health in the world.

The most frequent cancers of women are breast, cervix, colorectal and lung cancers, whereas in men are lung, prostate, stomach and colorectal cancers (66, 67). As a cause of death, cancer occupies the third place after cardiovascular and infectious diseases, but taking only developed countries it is generally the second cause of death after cardiovascular diseases (66, 67). Statistics for year 2002 shows 10.9 millions of new cases and 6.7 millions of deaths (3.796.000 men y 2.928.000 women), within a prevalence of 24.6 millions suffering from some kind of cancer this year (67). Among the cancers that caused most deaths were lung (1.179.000 deaths), stomach (700.000), liver (598.000) and colorectal (528.000) and among the most malignant, with less than 20% survival at 5 years, are those of lung, esophagus, stomach, liver and glioblastomas (66-68).

Cancer Treatment Using Specific Molecular Targets

The increased knowledge of cancer at the cellular and molecular level opened new treatment expectations addressing specific molecular targets and personalizing the approach according to oncogenic lesions.

Cancer cells derive from genetic damage that determines acquisition of new properties, diverging from normal behavior (69-71). In general, three kind of genes can lead to tumorigenesis: (i) oncogenes, (ii) tumoral suppressor genes (anti-oncogenes); y (iii) genes involved in genetic stability. Alterations in these genes result in the acquisition of a malignant phenotype characterized by the following abnormal properties: 1) Self-sufficiency in growth signals; 2) Insensivity to anti-growth signals; 3) Evading apoptosis; 4) Limitless replicative potential; 5) Sustained angiogenesis; 6) Tissue invasion and metastasis.

Despite of all these abnormal properties, cancerous cells become literally "addict" to the hyperactivity of a particular network of internal signals. This property is currently used to counteract their malignancy with drugs specially designed to inhibit the corresponding hyperactive network (61, 72). It is thus possible to obtain maximal benefits with minimal secondary effects, provided that the altered genes that sustain the hyperactive signaling network are susceptible to become identified in each tumor (17, 62, 73). Identification of genetic lesions is relatively advanced for some crucial signaling pathways, including those of the EGFR, thus allowing to personalize the use of drugs to specific targets, either as first line or in combination with chemotherapies. There is now a tendency and widespread consensus towards personalizing the cancer treatments in base of the knowledge of the crucial genetic lesions, as well as of the frequently altered molecular and biochemical processes that distinguish cancerous from normal cells (61, 69-72).

The EGFR Family

The EGFR is the paradigm of tyrosine-kinases that control cellular processes critical for the development and maintenance of the malignant tumoral phenotype. EGFR is member of the receptor tyrosine-kinase family compose by HER1/EGFR/ErbB1, ErbB2/HER2/Neu, ErbB3/HER3 and ErbB4/HER4 (3). The EGFR exhibits an extracellular domain that interact with ligands and an intracellular domain bearing the tyrosine-kinase domain. It is mainly localized in the plasma membrane where it is activated upon interaction with specific ligand stimuli, which leads first to its dimerization, followed by activation of its intracellular tyrosine-kinase. EGFR kinase activity phosphorylates tyrosines of the EGFR itself and several other intracellular substrates, thus initiating the signaling pathways that regulate processes of cell proliferation, survival and migration, all involved in tumorigenesis. The EGFR is one of the most ubiquitous receptors regulators of these processes and can be activated by different ligands, including EGF, HB-EGF and tumoral growth factor alpha (TGF-α) frequently secreted by tumoral cells (74). The EGFR is also trans-activated by a variety of stimuli of other receptors, especially receptors coupled to GTPases (GPCRs) (75). An interesting example is EGFR transactivation by extracellular nucleotides such as ATP that interact with $P2Y_1$ receptor, which is one of the more ubiquitous GPCR (64).

Alterations in the EGFR Associated to Cancer

Alterations in the function of the EGFR are frequently found associated to diverse cancers and the oncogenic effect of these alterations constitutes a preferred target for anti-cancer drugs (4, 21, 76). Almost 40-50% of solid tumors depend on an exacerbated activity of the EGFR tyrosine-kinase determined by genetic alterations.

A detailed recount of the EGFR genetic alterations include: (i) An increased number of EGFR gene copies leading to over-expression of the protein. Gliomas and lung tumors frequently exhibit such gene amplification (77, 78). However, other yet unknown mechanisms of EGFR over-expression exist without gene amplification, as can be seen in gastric cancer (79, 80).

EGFR over-expression is usually associated to higher malignancy; (ii) Mutations resulting in hyper-active EGFR; a) EGFRvIII mutant that by deletion lacks the extracellular region which conform the domain of ligand binding, being most important in glioblastomes (81); b) $EGFR^{L858R}$ mutant where leucine 858 is substituted by arginine and $EGFR^{DelE746-A750}$ mutant with deleted exon 19 that eliminates the conserved sequence LREA, both mutations affecting the tyrosine-kinase domain of the receptor (EGFR$^{TKDmut}$) and seen in 10-15% of non small cell lung cancer (NSCLC) (82, 83).

Drugs Currently in Use Against the EGFR for the Treatment of Certain Cancers

Cells bearing genetic alterations of the EGFR become "addict" to the exaggerated (oncogenic) signals arising from the receptor. Inhibition of EGFR exaggerated activity damages more cancerous than normal cells. Therefore, inhibitors of EGFR function now constitute the paradigm for developing targeted cancer therapies, which can be personalized after the identification of EGFR alterations in each tumor, thus optimizing the response to treatment (72, 84).

Two kind of drugs against the EGFR are currently in clinical use to treat certain cancers (4): (i) Monoclonal antibodies to the extracellular region of the EGFR that inhibit ligand binding (Cetuximab y Panitumumab). Cetuximab (erbitux; Merk KGaA, Darmstad, Germany; WO2009099649), is a monoclonal humanized antibody that binds EGFR with high affinity and competitively block ligand binding. It also induces endocytosis and negative regulation of the EGFR. It is mainly used to treat advanced colorectal carcinomas that express EGFR (85, 86); (ii) Small molecules that inhibit the tyrosine-kinase of EGFR, such as Erlotinib y Gefitinib (4) (WO03103676 y WO2005117887). These drugs compete with ATP for binding to the tyrosine-kinase domain, thus inhibiting the phosphorylation of EGFR substrates crucial for initiating the signaling cascades that promote exaggerated proliferation. Tyrosine-kinase inhibitors can be used to treat metastatic NSCLC and colon, head and neck and pancreas cancers (4, 87). Other patents of anti-tumoral drugs that inhibit EGFR function include WO 03097855, U.S. Pat. No. 5,795,898.

EGFR as Target for Personalized Therapies

The EGFR is one of the most studied and preferred targets for personalized cancer therapies (3, 61) (4). Two notable examples are NSCLC and colon cancer, in which the analysis of EGFR oncogenic mutations helps deciding whether tyrosine-kinase inhibitors can be conveniently used (88-90). In NSCLC, only 10-20% of patients respond to erlotinib or gefitinib (91, 92). Cetuximab is less effective (93). Responsive patients express EGFR$^{TKDmut}$ receptors bearing any of the mentioned mutations in the tyrosine-kinase domain, which not only provide oncogenic properties but also sensitize the receptor to the drugs (83, 94, 95). Identification of these mutants allows personalized treatments that can achieve close to 80-90% responses and improved survival (17, 89, 96-98).

Limitations of Available Anti-EGFR Drugs

The main limitation of current drugs that counteract the oncogenic function of EGFR are a relative low efficacy, as a great proportion does not respond, and development of resistance of initially sensitive tumors (17, 73, 87). For instance, those patients suffering from NSCLC that do not have depend on EGFR mutations that sensitize to erlotinib or gefitinib, which account for almost 85-90% of the cases, there is no much to offer. This is also true for other cancers that do not respond to these kinds of inhibitors. Furthermore, it is frequent to observe that even those initially sensitive patients that respond to erlotinib or gefitinib the tumoral growth recovers within periods of 6 months to 2 years. Almost 50% of these resistant tumors display a second mutation that substitutes methionine 790 for threonine in the tyrosine kinase domain, which block the interaction of the drugs with the ATP binding site (17). Recent studies report new drugs that now inhibit the EGFR T790M mutant (99). However, the possibility of resistance development to the new drugs still persists, as this is a common problem for kinase inhibitors (100). On the other hand, there are yet another 50% of cases that developed resistance but without the T790M mutation, in which the mechanism remains unknown (17, 101-103)

In summary, the evidence allows to conclude that the EGFR is a good target for designing anti-tumoral drugs but it is necessary to find alternative mechanisms for blocking its oncogenic function beyond those already in use, which relays on blockers of ligand binding or tyrosine-kinase activity (4).

The present invention proposes a novel strategy based on the pharmacologic induction of EGFR endocytosis and perturbation of EGFR endocytic trafficking using small drugs, leading to a decreased availability for becoming activated by external ligands and alterations in signaling location, which can be deleterious to EGFR-dependent cancerous cells (104).

EGFR Endocytosis as Target for Anti-Tumoral Drugs

Endocytosis has gained high preponderance among the variety of processes that control EGFR function (56-60), offering new anti-tumoral possibilities (104, 105). Mechanisms that control EGFR signaling are tightly entangled with those that regulate endocytic trafficking and cancerous cells can utilize such functional link to increase EGFR oncogenic activity (60, 106-111). Ligand binding leads to dimerization and activation of the intracellular tyrosine kinase activity of the EGFR, which then undergo transphosphorylation at several tyrosines that serve as recruiting motifs for downstream signaling elements (112). Tyrosine phosphorylated EGFR also becomes ubiquitinylated by the E3 ubiquitin ligase Cbl (113-115). Although the complex mechanism of ligand-induced endocytosis remains not entirely understood it seems to relay on redundant machineries involving a clathrin-adaptor AP2-interacting motif, ubiquitinylation and acetylation of the receptor (116). These structural/biochemical modifications define the endocytic trafficking of active EGFR (114, 116-118). Endocytosis provides a down regulation route involving ubiquitin-dependent and ESCRT-mediated EGFR sorting into intraluminal vesicles of multivesicular bodies that then fuse with lysosomes (117, 119, 120). However, depending on different factors, including ligand concentration (121) and receptor expression levels (104), activated EGFR can remain signaling-competent for variable periods of time before degradation, specifying different response outcomes. In cells overexpressing the EGFR, a common condition associated with higher malignancy, EGF stimulation leads to apoptosis through a mechanism that involves delayed sorting into the degradation pathway and the consequential increment in the endosomal pool of active EGFR (104, 105). Therefore, endocytic trafficking provides multiple opportunities to modify the intensity, location and duration of ligand-induced EGFR signaling, which in EGFR-dependent tumoral cells might have therapeutic potential.

However, pharmacologic induction of EGFR endocytosis leading to its removal from the cell surface has not been used before as anti-tumoral strategy for small drugs instead of antibodies, which frequently have limitations of accessing the cancerous cells within tumors.

We recently described a novel mechanism of control of EGFR endocytosis (122), which involves the signaling pathway of phosphatidic acid phosphohydrolase (PAP) enzymatic activity towards down-regulation of protein kinase A (PA/PKA pathway). This mechanism can be triggered by pharmacologic inhibition of PAP leading to increased PA levels, activation of type 4 phosphodiesterases (PDE4) and decreased cAMP levels and PKA activity, which determines the induction of EGFR endocytosis.

Signaling Phosphatidic Acid (PA)

PA mediates diverse cellular functions acting as structural and signaling element (123). Signaling PA derives mainly from hydrolysis of phosphatydilcholine by phospholipase D (PLD) (123), an enzyme activated by a large variety of extracellular stimuli (124-126), including EGF (127-129). Multiple cancers display elevated PLD activity or expression, which has been related with suppression of apoptosis and resistance to cancer treatments with inhibitors of mTOR (126, 130), a main regulator of phagocytosis (131). PA levels are down regulated by phosphatidic acid phosphohydrolases (PAP) producing diacylglycerol (DAG)(123).

Phosphatidate Phosphatases Activity (PAP) and Known Inhibitors

Two different kinds of enzymes hold PAP activity that converts phosphatidic acid to diacylglycerol. PAP1 are enzymes distributed among the cytosol and membranes of endoplasmic reticulum membranes, producing there the DAG necessary for the synthesis of triacylglycerols (TAG), phosphatidylcholine (PC) and phosphatidylethanolamine (PE). PAP1 activities are specific for PA and are $Mg^{2+}$-dependent and sensitive to inhibition by N-ethylmaleimide, comprising a family of three components: Lipin1, Lipin2 and Lipin 3 (1). PAP2, are transmembrane proteins mainly located at the plasma membrane and endosomal membranes, do not require $Mg^{2+}$ and are not inhibited by N-ethylmaleimide. PAP2 LPP are not specific for PA, hydrolyzing a broad range of other lipid phosphates, including lysophosphatidic acid (LPA), ceramide 1-phosphate (C1P), sphingosine 1 phosphate (S1P) and DAG pyrophosphate, all involve in signaling. Therefore, PAP2 are also called lipid phosphate phosphatases (LPP), comprising three related proteins named LPP1, LPP2 and LPP3 (1).

Several cationic amphiphilic compounds currently used in clinical practice for a variety of diseases have the capability to inhibit PAP as a side effect, including propranolol, desipramine, chlorpromazine, desmethylimipramine and trifluoroperazine (7-10).

Examples of Cancers with Different EGFR Oncogenic Alterations that can be Treated with PAP Inhibitors Lung Cancer About 30% of all cancer deaths are due to lung cancer, the leading cause of cancer death worldwide (132). About 90% of lung cancers are due to smoking affecting about 1.3 billion people in the world and it annually kills about 5 million people aged 30 or older (133). Cancers of non-small cell lung cancer (NSCLC) is one of the advanced malignant tumors with a major risk of death. Without treatment, patients with NSCLC and metastases have a median survival of 4-5 months. Only 10% of the patients survive the year. The standard first-line therapy for advanced or metastatic NSCLC is based on chemotherapy in combination with platinum-duplex, which increases the median survival to 8-11 months and the survival rate to about 30% at a year and 14-20% at two years (134).

Gastric Cancer

Gastric carcinoma is one of the most common epithelial-derived cancers (135). Its incidence has been declining over the past 50 years but still ranks the fourth in the frequency and the second after lung cancer as a cause of death, with significant differences between gender and ethnic groups. Each year about 1 million new cases are diagnosed and there are about 800,000 deaths from this cause. The survival rate at 5 years for patients with localized cancer is close to 60% while for those with metastases is only 2% (136). In cases of advanced disease, without treatment, the median survival is less than 12 months (often just 5.4 months). The new chemotherapeutic modalities have failed to lower the median survival that has remained largely unchanged over the past 10-20 years. There is no established chemotherapy for this cancer (79, 80, 137).

Glioblastomas

The "gliomas" include all tumors that are presumed to have glial cell origin and they are the most common tumors of the central nervous system. The grade III (anaplastic astrocytoma) and grade IV (glioblastoma) are considered to be malignant gliomas (68). Glioblastomas have a frequency of 3/100,000 people per year and they are among the most lethal tumors of all human cancers. The median survival of glioblastoma has been maintained for decades at about 9-12 months. Only 2% of patients 65 years and over and 30% of those under 45 survive 2 years, while about 75% die 18 months after diagnosis (138, 139). The invasive character and poor response to standard treatments including radiotherapy and chemotherapy contribute to the poor prognosis (139-141). The current treatment of radiotherapy and concomitant administration of temozolomide, followed by adjuvant temozolomide, increases the median survival of 12.1 months to 14.6 months (140).

SUMMARY OF THE INVENTION

The invention proposes to utilize PAP inhibitors to block the progression of cancers that depend on the epidermal growth factor receptor (EGFR, ErbB1/HER1), its oncogenic variants and other members of the ErbB/HER family of tyrosine kinase receptors (ErbB2/HER2, ErbB3/HER3 and ErbB4/HER4), currently used as suitable targets against cancer (2-5) and whose homo- and hetero-dimerization are crucial for normal and oncogenic functions (3, 6).

Among PAP inhibitors part of this invention are drugs previously used for other clinical purposes, unrelated between them, except for the fact of being cationic amphiphilic molecules (7-10). The present invention encompasses all known PAP inhibitors and all discovered in the future.

A specific example of the present invention corresponds to D-propranolol used alone or in combination with desipramine, both as described PAP inhibitors (9). D-propranolol combined with its enantiomer L-propranolol in a racemic mixture constitutes the drug known as propranolol (11, 12), a general beta-blocker that is used for treating hypertension and other cardiovascular disorders (13). However, only L-propranolol is useful as blocker of beta-adrenergic receptors (beta-blocker), which is the activity responsible for the anti-hypertensive effects. D-propranolol lacks beta-blocker activity at the clinical dosages of propranolol, as it is 60-100-fold less active than L-propranolol (11, 12). D-propranolol at higher doses has been experimentally used in the past for treating arrhythmia independently of beta-adrenergic blockage in humans (14). Desipramine has also PAP inhibitory activity (7, 15) but is currently used in clinics as a tricylic antidepressant that inhibits reuptake of norepinephrine and at less extension also serotonin (16).

The present invention demonstrates that a combination of D-propranolol with desipramine, both used as blockers of PAP activity, results useful for inhibiting the progression and causing death of cancerous cells that depend on the EGFR or its oncogenic variants, e.g. the oncogenic mutant $EGFR^{L858R/T790M}$ identified as resistant to anti-EGFR drugs in lung cancer (17) and the truncated EGFRvIII variant first described as highly malignant oncogen in glioblastomas (18).

As such, the invention represents a second use of known drugs previously used for other clinical purposes, which might be used in combination with D-propranolol. The invention also includes any other kind of PAP inhibitor that might be discovered or synthesized in the future, such as analogs of propranolol lacking beta-blocker activity. D-propranolol as single drug or in combination with presently known PAP inhibitors, as well as newly arising PAP inhibitors can be used alone or in combination between them or with anti-tumoral drugs having distinct mechanisms of action, including hormones, antibodies and drugs used in chemotherapy PAP inhibitors of present invention also can be used in combination with other kind of treatment, including surgery and radiotherapy, simultaneously of afterwards, similarly to other EGFR or ErbB2/HER2 function-interfering drugs (19, 20). PAP inhibitors would serve not only as complement to chemotherapy or to drugs directed to block EGFR function and its oncogenic variants (4, 21), but can also be the only available therapy once cancerous cells have developed resistance to drugs currently in use against the EGFR, a common problem in cancer treatment (17, 22).

The invention opens new possibilities for treating cancers that display oncogenic alterations, such as over-expression or mutations, of the EGFR or other members of its ErbB/HER family, including ErbB2/HER2, ErbB3/HER3 and ErbB4/HER4 (2, 4, 21), all functionally interrelated through heterodimerization (3, 6).

Among these are the cancers of lung (17), breast (23), colorectal (24, 25), head and neck (26, 27) and pancreas (28), to which drugs that interfere with the oncogonic action of EGFR or ErbB2/HER2 have already been approved for treatment (4, 5, 20).

The invention also include ovarian (29-34), stomach and esophagus (35-38), hepatic (39, 40) and prostate (41, 42) cancers, as well as melanomas (43-51) and glioblastomas (52-55), cancers where EGFR, EGFR mutants such as EGFRvIII, alterations of other ErbB/HER members, such as ErbB2/HER2, ErbB3/HER3 or ErbB4/HER4, can contribute to malignancy, even though drugs that interfere with their oncogenic function have had uncertain beneficial effects or are still under study.

The invention encompasses the following fields:
1) The biology of cancerous cells, which is determinant in the pathogenicity of cancer, frequently involving oncogenic signaling functions of EGFR and members of its family of tyrosine kinase receptors (ErbB/HER). Such alterations enhance the aggressiveness and malignancy of tumoral cells and are also crucial for their growth, survival and progression towards metastatic stages, thus offering an effective target for designing novel anti-cancer strategies, as proposed by this invention;
2) Endocytic trafficking, which plays a crucial role in the normal and pathogenic functions of the EGFR and other members of its ErbB/HER1-4 family;
3) The function of the PA/PKA (Phosphatidic acid/protein kinase A) signaling pathway, which has been almost unknown since the demonstration in the present invention that is involved in the regulation of EGFR endocytic behavior and constitutes one of the fundaments of the present invention.
4) The use of PAP inhibitors for treating cancer. This has not been previously proposed.
5) Second use for drugs that are already known and have been used for other clinical purposes based on mechanisms of action distinct from PAP inhibition. For instance, D-propranolol has been experimentally used in the treatment of arrhythmia, while desipramine is currently use is anti-depressive treatments as blocker of noradrenalin recapture.

The fundament of the present invention involves all these fields intertwined with the novel function discovered for the PA/PKA signaling pathway and the novel regulation mechanisms that determine the cell surface levels and endocytic trafficking/signaling of EGFR. These regulation mechanisms are susceptible of pharmacologic manipulation, with the aim of: 1) Inducing endocytic removal of the EGFR from the cell surface, thus decreasing its availability to activation by a variety of external stimuli; 2) perturbing the endocytic trafficking of already ligand-activated EGFR, thus changing the main subcellular location and duration of intracellular signaling. This translates in deleterious effects upon cancerous cells that depend on these signals for proliferation, migration and survival.

The invention consists in the use of PAP inhibitors, such as D-propranolol and desipramine, and other drugs originally used for other purposes, to design novel anti-cancer therapies based on their induction of EGFR removal from the cell surface by endocytosis, as well as perturbing endocytic trafficking/signaling of activated EGFR, which also includes the other ErbB/HER family members that form hetero-dimmers with EGFR. This strategy has not been used previously with small drugs.

Advantages of the Invention

The present invention proposes a distinct strategy from those currently in use to reduce the progression of EGFR-dependent or ErbB/HER-dependent cancers. To interfere with the oncogenic role of these tyrosine-kinase receptors in cancer, drugs already in clinical use and those in study are directed against the molecule of the receptor or its ligands. These drugs consist either of humanized monoclonal antibodies (e.g. cetuximab and panitubumab) that block the receptor interaction with external ligands (EGF, EGF-HB, etc), increase receptor endocytosis and promote recognition by immune effector cells, or small drugs (e.g. erlotinib and gefitinib) that block intracellular tyrosine-kinase activity (2-5). Both strategies decrease the generation of oncogenic signals from an activated EGFR. In contrast, the compounds proposed in the present invention do not have the molecule of the EGFR as direct target but instead molecules involved in the regulation of its cell surface accessibility and signaling location through the endocytic machinery.

The present invention proposes to block the phosphatidic acid phosphohydrolase (PAP) activity as strategy to induce the removal of EGFR from the cell surface through endocytosis and to perturb the endocyitc traffic crucially involved in signaling of activated EGFR (56-60). Such strategy fits into the present tendency of targeted treatments directed to counteract mainly the signaling pathways altered in cancerous cells, thus causing minimal deleterious effects in normal cells (4, 61).

Another advantage is the availability of several molecules with known structure that share the capability of PAP inhibition, including propranolol, desipramine, chlorpromazine, desmethylimipramine and triofluoroperazine (7-10), thus providing structural information for designing a novel family of PAP-inhibitors potentially useful to combat cancerous cells.

At the same time the present invention introduces a previously unknown mechanism for counteracting the oncogenic function of the EGFR and other ErbB/HER members with which it forms heterodimers, being useful for the treatment of cancers whose malignancy depends on their oncogenic function, thus being a complement of treatments already in use or the only alternative when these treatments are no longer effective.

An additional and important advantage is the selectivity of the approach involving the oncogenic function of the EGFR and ErbB/HER members, thus offering the opportunity to personalize the treatments according to known molecular markers, as well as to others that might be discovered in the future for this particular treatment, which can be analyzed in each case, optimizing the use of drugs upon cancers with higher probabilities of response (17, 25, 62). The application of PAP inhibitors restricted to cancers that present oncogenic alterations of the EGFR and other ErbB/HER members (overexpression or mutations) has clear economic advantages.

Finally, the use of compounds that act upon PAP enzyme activity, not directly involved in carcinogenesis, in contrast to the EGFR and ErbB/HER members whose alterations can directly promote cell transformation and progression towards malignant cancerous phenotypes, might delay or eventually avoid development of resistance to treatment, a main problem for drugs that target oncogenic kinases, including the tyrosine-kinase of the EGFR (17, 22, 63).

DETAILED DESCRIPTION OF THE INVENTION

Figure 1:
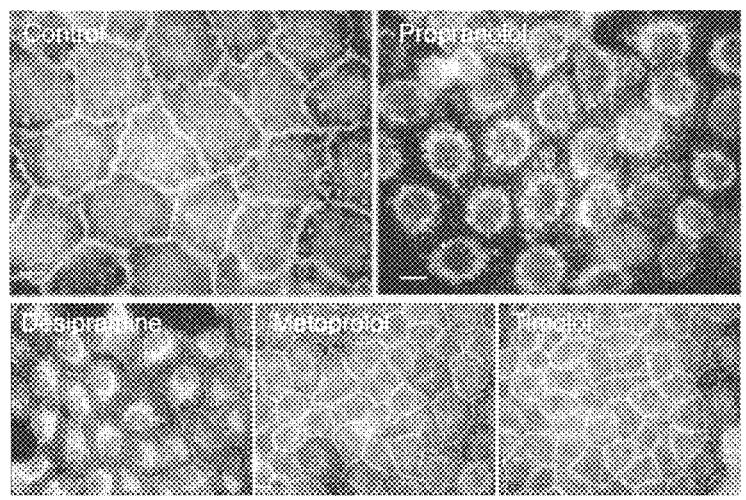
FIG. 1: Propranolol and desipramine induce endocytosis of the EGFR in cultured tumoral cells. The image illustrates the immunofluorescent pattern of the EGFR in HeLa cells incubated in the absence or presence 75 µM propranolol, 75 µM desipramine, 50 µM metoprolol or 50 µM timolol.

The present invention describes the inhibition of PAP with D-propranolol alone or combined with desipramine as a novel strategy, based on endocytic induction, to block growth of cancerous cells that depend on the EGFR or its oncogenic variants.

Propranolol (which represents the racemic mixture of D and L propranolol) has been used as beta-clocker for experimental attenuation of tumor growth and metastasis of cancerous cells that express beta-adrenergic receptors, and thus such use is focused on its active principle L-propranolol, instead of D-propranolol. In these experiments, propranolol only prevents the beta-adrenergic stimulus presumed to promote tumorigenesis by stress conditions, and is expected to counteract the malignant properties promoted by intense sympathetic tone (142-144). In fact, propranolol is not currently included in approved treatments against cancers whose malignancy depends on the oncogenic activity of EGFR or other ErbB/HER family members. D-propranolol has not been previously used in any publication for counteracting cancer cell growth.

Regarding desipramine, which is used in this invention as an example of PAP inhibitor that can be combined with D-propranolol for more effective anti-cancer effects, it is mentioned in the international publication WO 2006/017185 among several other compounds described to display anti-proliferative effects in vitro. However, this publication does not refer to any mechanism by which desipramine might be causing a decrease in cell proliferation, does not analyze whether such an effect is selective or also affect normal cells. This publication does not allow to visualize possibilities of effective use in anti-tumoral therapies or optimization of the effects. The international publication WO 2008/112297 describe inhibitors of the enzyme acid sphingomielinase among which appears desipramine as analogous compound, predicting that it might have anti-cancer effects, but no specific results are reported.

Desipramine used as tricylic antidepressant that inhibits reuptake of norepinephrine and serotonin (16) has been reported to decrease (145-149) growth and survival of cancerous cells in culture. The reported doses are relatively high, 40-100-fold higher than those used in the present invention. At such high concentrations desipramine is rather toxic for most kind of cells, both tumoral and normal cells. Furthermore, none of these studies have considered a dependency of EGFR or the possibility of acting through PAP inhibition. In the present invention desipramine is an example of PAP inhibitor that can improve the anti-cancer properties of D-propranolol acting at concentrations close to those reported in patients. The combination of D-propranolol (10-30 microMolar) and desipramine (1 microMolar) at concentrations close to those achieved in the blood by patients treated for arrhythmia (14) or depression (150, 151), respectively, is selective for tumoral cells that depends on the oncogenic activity of EGFR or its mutants (See FIGS. 2 and 3).

The inventors of the present invention have published that propranolol as racemic mixture or L- and D-propranolol induces endocytosis of EGFR, showing that the mechanism involves PAP inhibition, an increment of PA and a subsequent increase in the activity of type 4 phosphodiesterases, leading to a decreased cAMP levels and a decreased PKA activity (122). This novel control system gives the possibility to use different enzymes of the PA/PKA pathway, including PAP, as novel targets to induce EGFR endocytosis and decrease the growth of tumors whose malignancy depends on oncogenic EGFR function.

The inventors of the present invention had previously demonstrated that inhibiting the basal PKA activity in the absence of EGF leads to internalization of empty/inactive EGFR, whereas in the presence of EGF retards the degradation kinetics of ligand-activated EGFR due to delayed sorting into the lysosomal degradation pathway (152).

It is then possible to pharmacologically induce EGFR internalization and not only decrease their accessibility to stimuli but also perturb EGFR intracellular trafficking and signaling, through decreasing the PKA activity via the PA/PDE4/cAMP/PKA pathway triggered by PAP inhibitors. This PA/PDE4/cAMP/PKA signaling pathway has been previously described but its function had remained unknown (15). The investigator's results indicate that this PA/PDE4/cAMP/PKA signaling pathway regulates the cell surface levels and intracellular trafficking of EGFR acting upon the endocytic and recycling machinery (122).

The invention is also based on the following additional observations: 1) The enantiomer D-propranolol, which lacks the beta-blocker activity of L-propranolol, and desipramine, both used as inhibitors of PAP, induce EGFR endocytosis; 2) D-propranolol and desipramine inhibit the proliferation of cancerous cells expressing oncogenic alterations of EGFR, including EGFR over-expression and the EGFRvIII mutant. The effect of these drugs is selective to malignant cells, leaving non-tumoral cells relatively unaffected or weakly affected. Their combination is clearly better than each drug alone.

D-Propranolol and desipramine used as PAP inhibitors (15), activate the PA/PDE4/cAMP/PKA signaling pathway that induces EGFR endocytosis and intracellular accumulation (122). The invention of using D-propranolol alone or in combination with desipramine is completely distinct from their previous use in clinical treatments. It is also distinct from the use of the racemic mixture propranolol to treat hypertension and other vascular disorders that require beta-blocker activity, only provided in the mixture by L-propranolol and not by D-propranolol. D-propranolol has been experimentally used in humans as anti-arrhythmic lacking beta-adrenergic blockade (14), whereas desipramine is a tricylic antidepressant that inhibits reuptake of norepinephrine and to a less extent also serotonin (16).

In cell biology, propranolol is currently used as PAP inhibitor to study the function of PA and diacylglycerol in a variety of cellular processes, such as signaling, protein trafficking and cytoskeletal functions (123).

Among the variety of signaling pathways where PA participate, the activation of PDE4 has been the less studied. Activation of PDE4 by PA leads to decreased levels of cAMP and consequently to decreased activity of PKA, effects that are evoked by propranolol, independently of its beta-blocker effect, and by desipramine, independently of its effect upon noradrenaline recapture (15, 153).

D-propranolol and analogs lacking beta-blocker activity, alone or in combination with desipramine, could be used as PAP inhibitors to complement treatments based on chemotherapies or EGFR inhibitors (e.g. cetuximab, erlotinib and gefitinib) and also as single therapy when resistance to current treatments has already develop.

The invention opens new possibilities for the treatment of cancers whose malignancy depends on oncogenic alterations of EGFR or other ErbB/HER family members that form heterodimers with EGFR, such as ErbB2/HER2, ErbB3/HER3 and ErbB4/HER4. These include cancers of lung (17), breast (23), colorectal (24, 25), head and neck (26, 27) and pancreas (28), for which drugs that interfere with the oncogonic action of EGFR or ErbB2/HER2 have already been approved for treatment (4, 5, 20). Other cancers shown to derive their malignancy from EGFR, EGFR mutants such as EGFRvIII, alterations of other ErbB/HER members, such as ErbB2/HER2, ErbB3/HER3 or ErbB4/HER4 include ovarian (29-34), stomach and esophagus (35-38), hepatic (39, 40) and prostate (41, 42) cancers, melanomas (43-51) and glioblastomas (52-55).

EXAMPLES

Example 1

Comparative Assessment of L-, D-Propranolol and Desipramine Effects on EGFR Internalization Measured by $^{125}$I-EGF Binding and Visualized by Immunofluorescence The inventors have described that the racemic mixture of L and D propranolol decreases in just 30 min the levels of EGFR at the cell surface, reaching 80% at the highest doses (300 µM), as reflected by decreased $^{125}$I-EGF binding (122), with an effective concentration 50% ($EO_{50}$) of about 75-100 µM.

The effect of propranolol as inhibitor of PAP, proposed by the present invention for blocking the oncogenic action of EGFR, requires higher concentrations than those as beta-adrenergic blocker in vitro (143, 144). L-propranol is almost a 100-fold more potent beta-adrenergic blocker than D-propranolol. However, the results of the inventors demonstrate L-propranolol and D-propranolol are equivalent in their capacity of reducing the cell surface of EGFR (FIG. 1, A), both with an $EC_{50}$ of about 75-100 µM, similar to that reported for the racemic mixture (122).

Desipramine is also effective inducing a decrease in $^{125}$I-EGF binding, with $EC_{50}$ of about 20 µM (FIG. 1B). A combination of $EC_{50}$ for desipramine (20 µM) and propranolol (75 µM) decreases 75-80% of EGFR from the cell surface, as assessed by $^{125}$I-EGF binding assay (FIGS. 2C y D).

Indirect immunofluorescence of FIG. 1E shows that 75 µM of either D- or L-propranolol induce redistribution of EGFR from the cell surface to an intracellular predominantly perinuclear location, which has been defined as recycling endosomes by its co-localization with transferrin, a marker for these kind of endosomes (122). This effect is not due to the beta-blocking activity because D-propranolol is 60-100-fold less active than L-propranolol as beta-blocker, while both D- and L-propranolol are equivalent in inducing the PA/PKA pathway (15) as well as EGFR endocytosis, as shown in FIG. 1A. Desipramine that also has an inhibitory effect upon PAP activity (15, 153) mimics the endocytic effect of propranolol.

The invention is valid for any known PAP inhibitor that can be used in combination with propranolol or for new PAP inhibitors that might have even higher effectiveness and can be used alone. The results shown here are only an example, which does not restrict or limit the field of the invention.

Example 2

Figure 2:
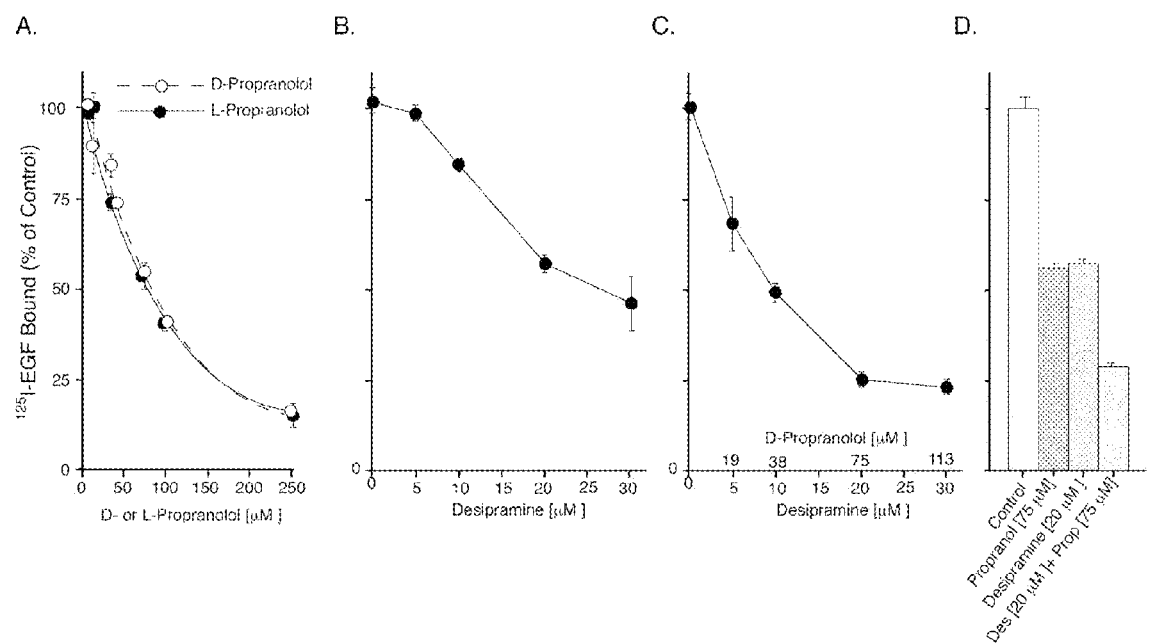
FIG. 2: The enantiomers L-y D-propranolol as well as desipramine decrease the cell surface availability of the EGFR assessed by radioligand binding. A. L-y D-propranolol; B. desipramine; C. Combination of different concentrations of D-propranolol (upper scale) with desipramine (lower scale); D. Combination of $EC_{50}$ of D-propranolol and desipramine.

Tumor Cell Models with Different Proliferation Rates Dependent on EGFR and its Oncogenic Variant EGFRvIII The effectiveness of D-Propranolol and Desipramine as inhibitors of proliferation and viability of tumor cells dependent on EGFR is demonstrated in glioblastoma cells in culture. The cell line from human glioblastoma, U87, expresses low levels of EGFR (data not shown) and when transfected to overexpress the mutant EGFRvIII the rate of proliferation increases enormously (FIG. 2). These cells provide an appropriate experimental model to test the drugs. The other model system used was from glioblastoma multiform cells, derived directly from a patient (GBM1), that express high levels of EGFR but not EGFRvIII. The sensitivity to the combination of D-Propranolol and Desipramine is greater in the U87-EGFRvIII cells as well as in GMB1 cells compared with U87 cells. Concentrations as low as 2 µM D-propranolol (only double of that reported in plasma of patients under treatment with propranolol for hypertension) together with 0.6 μM Desipramine (half of that described in plasma) achieve remarkable effects in U87-EGFRvIII cells, without greatly affecting the cells that do not express this oncogenic mutant (FIG. 2A).

Concentrations of D-propranolol of 10 μM have been reported in the blood of patients under treatment for arrhythmia (14) measured 12 h after the last doses. The effect of 10-30 μM D-propranolol, which likely reflect a range of concentrations close to those generated during clinical use in patients with arrhythmia, were used either alone or in combination with 1 μM desipramine, the reported effective blood concentration for this drug. These higher doses of 10-30 μM D-propranolol alone or combined with 1 μM desipramine have similar selective effects (FIG. 2B).

These results demonstrate effectiveness of D-propranolol in combination with desipramine for tumoral growth that depends on the oncogenic contribution in cells that overexpress either EGFR or its truncated variant EGFRvIII. The surprising effect of the combination of both drugs makes it possible to use clinically accepted doses for cancers that express the EGFRvIII.

Example 3

Anti-Cancer Effects of D-Propranolol and Desipramine on Several Cancerous Cell Lines As a control of selectivity, the experiment shows that MDCK cells, a canine kidney epithelial cell line that expresses low levels of EGFR and that are not malignant (64), are not affected by the drugs. Instead, the highly malignant mice melanoma cells B16F10, which belongs to the B16 strain of melanoma cells reported to depend on EGFR and ErbB3 and widely used for studies of anti-EGFR drugs (154-156) and the human lung cancerous cells H1975 that express the oncogenic double mutant EGFR$^{L858R/T790M}$ (101), are the most sensitive. Of note, the EGFR$^{L858R/T790M}$ is resistant to the tyrosine-kinase inhibitors erlotinib or gefitinib in clinical use (157). The drugs are also effective against the ovarian cancer cells UCI101 also reported to express EGFR (158).

In summary, the D-Propranolol (and analogs that lack beta-blocker activity) and Desipramine, alone or in combination are useful for the treatment of cancers whose malignancy depends on oncogenic alterations of the EGFR, given either by over-expression (such as BMB1) or by mutations (e.g., EGFRvIII).

The scope of the invention extends to cancers that express other oncogenic EGFR variants, such as those described in lung cancer, or even other family members (e.g., ErbB2/Neu, ErbB3/HER3 and ErbB4/HER4), and other inhibitors of known PAP inhibitors (Sphingosine and Chlorpromazine) to combine with D-propranolol, or new PAP inhibitors that might display higher effectiveness as to be used alone.

D-propranolol is a reported PAP inhibitor (153), which can be used in humans at higher doses than propranolol, the beta-blocker racemic mixture that is currently used for the treatment of hypertension and other vascular disorders. At least 10-fold higher concentrations of D-propranolol than the racemic mixture can be reached in blood without major collateral problems, as reported in patients treated with D-propranolol to control arrhythmia (14). In these patients the concentration in the blood assessed 12 hours of the last dose is close to 10 μM (14). Because the concentration of propranolol in circulation decreases with half-time of about 4-6 hours, and thus the patients have to be treated four times a day to achieve clinically relevant blood concentrations, it might be expected that the concentration of 30 μM used here would be well tolerated.

Furthermore, combinations of D-propranolol and desipramine can be more effective than each drug alone for treating cancers that depend on the oncogenic stimulus of EGFR or its oncogenic mutants.

DETAILED DESCRIPTION OF THE FIGURES

FIG. 1: The enantiomers L- and D-Propranolol and Desipramine reduce the availability of EGFR at the cell surface determined by radio ligand binding and this effect is due to endocytosis: HeLa cells previously deprived of serum for 4 hours were treated for 30 min with the indicated doses of the different drugs and then a radio ligand binding assay was performed incubating the cells with 20 ng/ml $^{125}$I-EGF at 4° C. for 1 hour, to detect the EGFR at the cell surface. A. L- and D-Propranolol caused a drop in the binding of $^{125}$I-EGF reflecting a decrease of about 50% of EGFR at the cell surface at a concentration of 75 μM (EC$_{50}$) and 80% at 250 μM. The effects of L- and D-Propranolol are indistinguishable; B. Desipramine also induced a drop in the levels of radio ligand binding, with EC$_{50}$ ~20-25 μM; C. Combination of different concentrations of D-Propranolol (upper scale) and Desipramine (lower scale); D. Combination of D-Propranolol (75 μM) and Desipramine (25 μM) used in their respective EC$_{50}$ caused a ~75% decrease in the binding of $^{125}$I-EGF. E. Indirect immunofluorescence with the anti-EGFR monoclonal antibody HB8506 (ATCC hybridome) on HeLa cells grown on cover slips and treated for 30 min with 100 μM D- or L-propranolol and 20 μM desipramine. Control cells show most of the EGFR staining at the borders indicating cell surface distribution, while with all the drugs the pattern changed to an intracellular location, mainly at the perinuclear region.

FIG. 2: D-propranolol and desipramine reduce proliferation of tumoral glioblastoma cells that depend on EGFR (GBM1) or EGFRvIII (U87-EGFRvIII)

A. U87 and U87 transfected to overexpress the oncogenic mutant EGFRvIII (U87-EGFRvIII) as a model of tumor cells with different proliferation rates. 10,000 cells were seeded in 24-well plates with MEM medium supplemented with 10% FBS and antibiotics (Penicillin 100 U/ml and Streptomycin 100 mg/ml). The U87 cells permanently transfected with plasmid pcDNA3-EGFRvIII-myc (U87-EGFRvIII) show higher proliferation than U87 cells.

B. U87-EGFRvIII and GBM1 cells from a patient with glioblastoma that overexpress EGFR but not EGFRvIII are selectively sensitive to D-propranolol and desipramine. After seeding 10,000 cells (U87, U87-EGFRvIII, and GBM1) per well and cultured for 18 hrs, the culture medium was replaced without (control) or with the indicated drugs, 10 μM D-Propranolol (D-Prop) and 1 μM Desipramine (Des), either alone or in the combination of both, changing the medium every 24 hours for 4 days. While the U87 cells are not sensitive to the drugs, both U87-EGGFRvIII and GBM1 decrease their proliferation in the presence of the drugs with higher effect of the drug combination.

Figure 3:
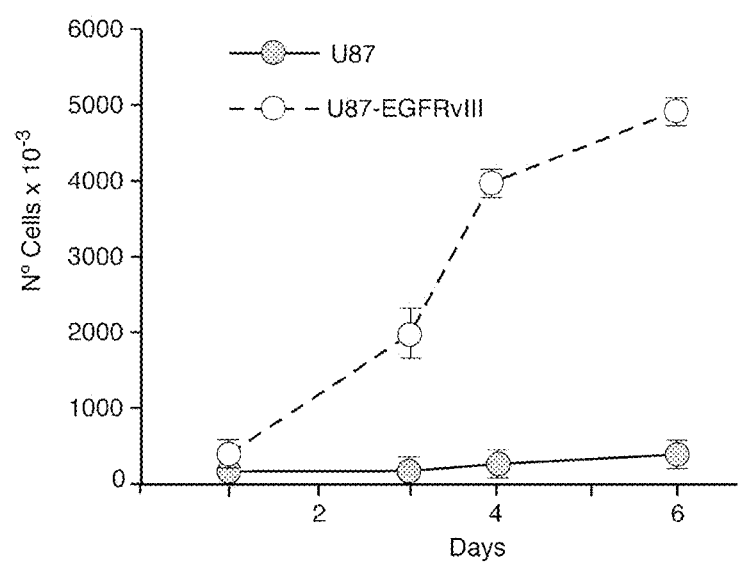
FIG. 3: Glioblastoma cells U87 and U87 transfected to overexpress the oncogenic mutant EGFRvIII (U87-EGFRvIII) as tumoral models with different proliferation rates.

FIG. 3: D-propranolol and desipramine selectively impair the proliferation of tumoral cells After seeding 10,000 cells per well and cultured for 18 hrs, the culture medium was replaced without (control) or with the indicated drugs, 10 or 30 μM D-Propranolol (D-Prop) and 1 μM Desipramine (Des), either alone or in the combination of both, changing the medium every 24 hours for 4 days. Viable cells counted in an automatic cell counter after incubation with vital tripan blue dye are represented as % of live cells respect to untreated controls. Tumoral ovarian cells (UCI 101), melanoma (B16F10) and non small cancer lung cells (NSCLC; H1975) are all sensitive to the drugs whereas Madin-Darbi-canine kidney (MDCK) cells that are not tumoral and express very low levels of EGFR are not affected, neither by D-propranolol nor by desipramine.

Figure 4:
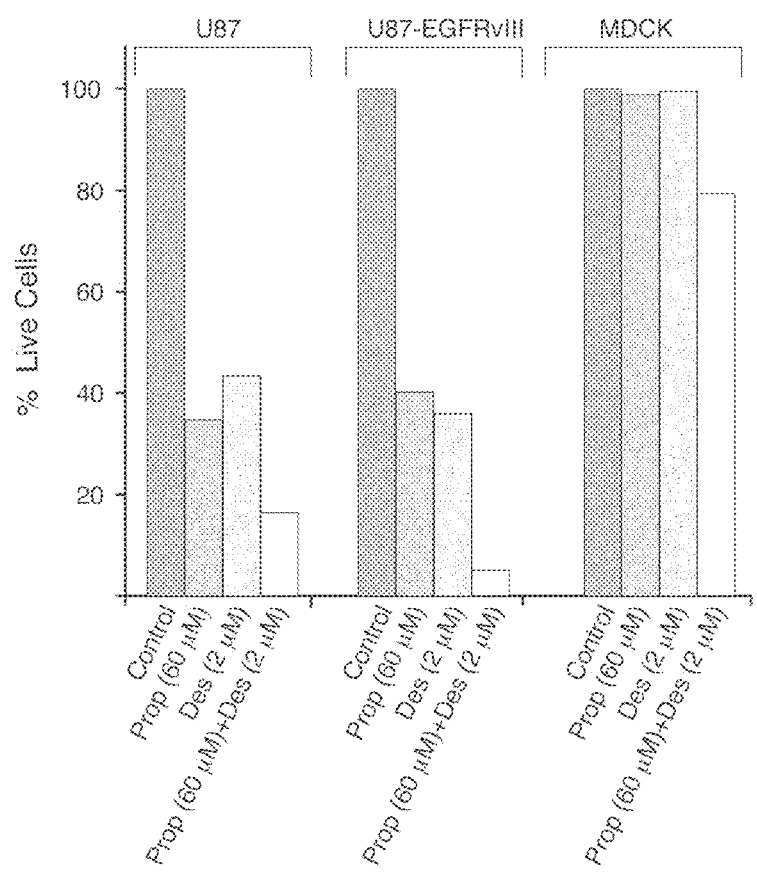
FIG. 4: Effect of D-propranolol and desipramina added as continuous treatment on the viability of glioblastoma cells U87 and U87-EGFRvIII and not-tumoral epithelial cells MDCK.
Figure 5:
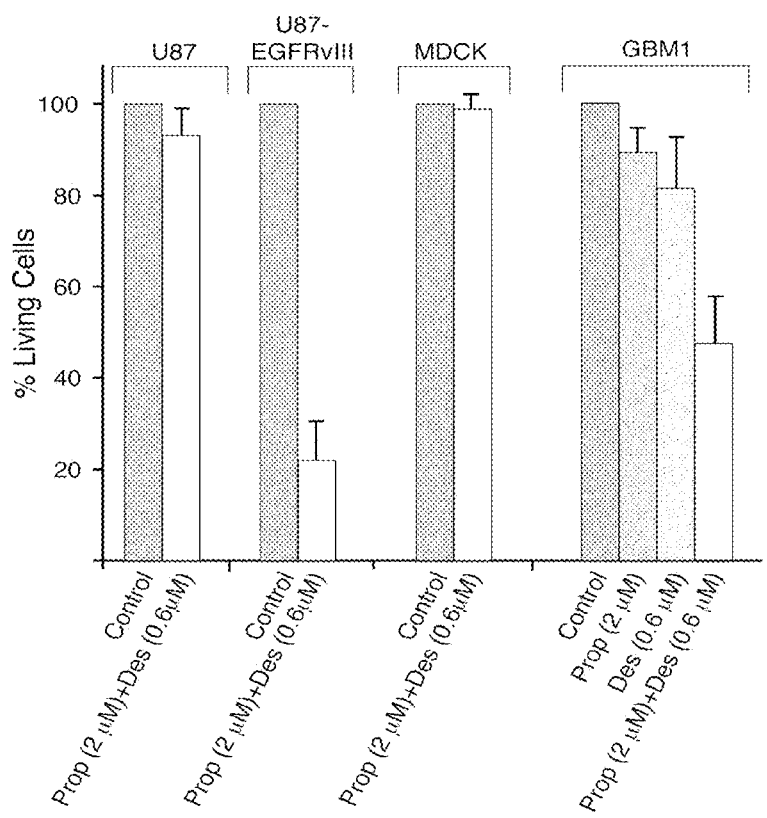
FIG. 5: Continuous treatment with low concentrations of D-propranolol (D-Prop) and desipramine (Des), both alone and in combination, selectively inhibits the enhanced proliferation of U87-EGFRvIII and tumoral cells in primary culture from a patient with glioblastoma (GBM1) that overexpress EGFR.
Figure 6:
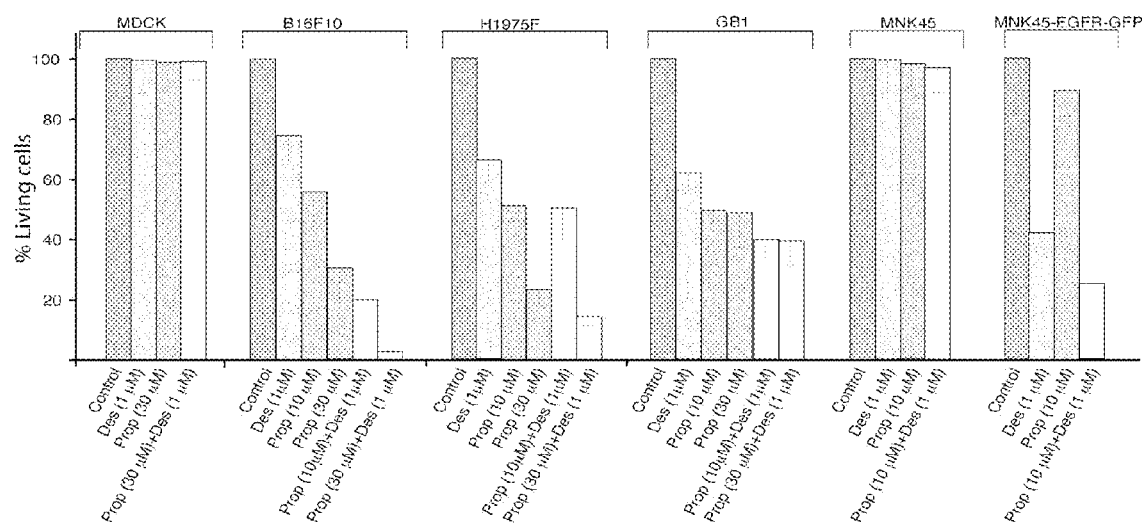
FIG. 6: Continuous treatment with two concentrations (10 and 30 µM) D-propranolol, close to those found in blood of patients treated for arrhythmia, used alone or in combination with 1 M desipramine selectively inhibits the proliferation of several tumoral cell lines and tumoral cells in primary culture from a patient with glioblastoma (GBM1) that overexpress EGFR.
Figure 7:
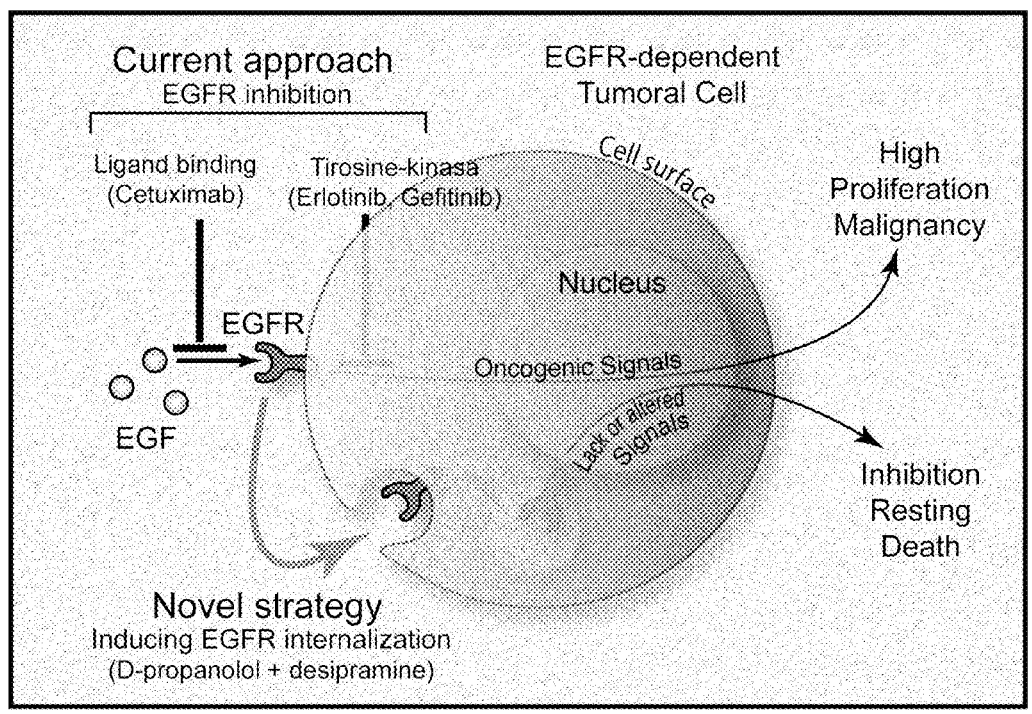
FIG. 7: Novel treatment strategy for EGFR-dependent cancers based on the effects of D-propranolol and desipramine.

FIG. 4: New strategy for treatment of EGFR-dependent cancers based on the effects of D-Propranolol and Desipramine: In contrast to current strategies that are directly targeting the EGFR molecule, attempting to inhibit ligand binding or tyrosine kinase activity, the invention proposes to induce the endocytosis of the receptor mediated by drugs that inhibit PAP and activate the PA/PKA signaling pathway, thereby inducing a relocation of EGFR from the cell surface to endosomes.

Description of Techniques

Reagents and Antibodies

Recombinant human EGF was purchased from Invitrogen (Carlsbad, Calif.), protein A-Sepharose, propranolol and high glucose DMEM from Sigma-Aldrich (St. Louis, Mo.), fetal bovine serum from Hyclone Laboratories (Logan, Utah), cell culture reagents from Invitrogen and Sigma Aldrich, plastic plates for tissue culture from Nalge Nunc (Naperville, Ill.). The culture medium of hybridoma HB8506 purchased from the American Type Culture Collection (ATCC, Manassas, Va.) was used as a source of monoclonal antibodies against the extracellular domain of human EGFR. The rabbit monoclonal antibody against the carboxyl terminal domain of EGFR was purchased from Millipore.

Construction of Plasmid for the Expression of EGFRvIII Oncogene

EGFR cDNA cloned into the pBK-CMV vector between HindIII and Smal sites described in (152) was used for constructing the expression vector for oncogenic variant EGFRvIII. First, PCR fragments corresponding to exons 1-2 and 7-28 were obtained using primers containing restriction sites for Kpnl and EcoRV for the first fragment and EcoRV and Xbal for the second fragment. After ligating these fragments a new fragment was obtained corresponding to EGFRvIII that lacks exons 2-7 and then was cloned between Kpnl and Xbal sites in pcDNA3.1 and pcDNA3.1 myc vectors, obtaining the vectors pcDNA3-EGFRvIII and pcDNA3-EGFRvIII-myc, respectively. Both constructs were analyzed by sequencing.

Cell Culture and Transfection

HeLa cells used for the radioligand binding assays and immunofluorescence to study EGFR endocytosis have been characterized previously in our laboratory (64, 122, 152). The cells were grown to approximately 80% confluence and maintained without serum for 4 h before testing. U87 human hybridoma cells from the ATCC were grown and transfected with pcDNA3.1-EGFRvIII-myc using the lipofectamine method following the manufacturer's instructions (Invitrogen). 100,000 U87 cells were seeded in 15 mm plated and after 48 hours of seeding cells were transfected with 1 μg of plasmid pcDNA3-EGFRvIII-myc. After 48 hours post-transfection the selection medium (DMEM, 10% Fetal Bovine Serum (FBS) supplemented with antibiotics (100 IU/ml penicillin, 100 mg/ml streptomycin) and 0.8 mg/ml Geneticin was added (G418, Sigma). After 2 weeks in selection media, permanently transfected cells were obtained (U87-EGFRvIII).

GBM1 cells were obtained from a biopsy specimen from a patient diagnosed with glioblastoma multiforme. The biopsy specimen of the tumor was approximately 1 cm. It was washed 4 times with PBS, cut in pieces and incubated in PBS with 0.125% trypsin, 5 mM EDTA for 15 min at 37° C. with continuous agitation. After mechanical disruption with a Pasteur pipette, cells were centrifuged at 1200 rpm for 10 min in a tabletop centrifuge. The pellet was resuspended 2 ml of PBS with ovomucoid inhibitor (1 mg/ml) and DNase I (1 mg/ml) and then re-centrifuged again for 10 min at 1200 rpm. The cells were resuspended in NH4Cl/Tris pH 7.2 and incubated for 5 min at 37° C. (5 ml to 50 million cells), pelleted by centrifugation for 10 min at 1200 rpm, and finally resuspended and cultured in DMEM with 10% FBS. These cells were maintained for at least 10 passages.

Evaluation of Proliferation and Viability of Cultured Tumor Cells In Vitro and Treatment with D-Propranolol and Desipramine Cells were seeded at a density of 10.000 cells per well in 24-well plates in triplicate and cultured in DMEM supplemented with 10% FBS and antibiotics (penicillin 100 U/ml and streptomycin 100 mg/ml). The medium with the drugs was changed each 24 hours. The respective controls received only culture medium. Viable cells were counted after 4 days of treatment in an automatic cell counter (Countess, Invitrogen) after incubation with vital tripan blue dye and are represented as % of live cells respect to untreated controls.

Indirect Immunofluorescence and Colocalization Analysis

HeLa cells grown on glass coverslips were washed three times with cold phosphate buffer saline (PBS) and incubated 2 h in serum free DMEM-HEPES media at 37° C., in order to accumulate EGFR on the cell surface. Then the cells were washed with PBS and fixed for 30 min at room temperature with 4% paraformaldehyde in PBS supplemented with 0.1 mM CaCl2 and 1 mM MgCl 2 (PBS-CM). After washing three times with PBS plus 0.2% gelatin (300 Bloom, Sigma Aldrich, PBS-CM-G), 5 minutes each time, cells were permeabilized with 0.2% Triton X-100 for 10 minutes at room temperature and incubated for 12 h at 4° C. with anti-EGFR monoclonal antibody (mAb) HB8506. After at least 6 washes in PBS-CM-G cells were incubated with secondary antibody anti-mouse IgG coupled to Alexa488 (dilution 1/1000) for 30 min at 37° C. Fluorescence digital images were obtained on a Zeiss Axiophot microscope with an oil immersion objective Plan-Apochromat 63X/1.4 and Zeiss Axiocam camera and transferred to 14 bits at a computer workstation running imaging software AxioVision (Zeiss, Thorn-wood, NY) as described (159).

Ligand-Binding Assays and Endocytic Rate Constants

The radioligand $^{125}$I-human EGF was prepared by the chloramine T method as described (122, 152, 160) yielding specific activities of 50000-70000 cpm/ng. Binding assays were performed in Hanks solution with 20 mM HEPES and 0.2% bovine serum albumin (BSA) for 1 h at 4° C., as described (122). HeLa cells deprived of serum for 4 h were treated for 30 min with the indicated doses of various drugs and then incubated with 20 ng/ml $^{125}$I-EGF at 4° C. in binding medium (MEM-Hank's, 25 mM HEPES, 0.2% BSA RIA grade), stirring for 1 h. The cells were lysed with 1 N NaOH for 2 h at room temperature and the counts per minute of each sample in triplicate was determined in a gamma counter, including a nonspecific binding point obtained by incubation with an excess (500 fold) of cold ligand, whose value was subtracted from each sample. The radioligand binding in saturating condition provides an estimate of the amount of EGFR on the cell surface.

Summary of the Invention of a Novel Strategy for Cancer Treatment

Epidermal growth factor receptor (EGFR) belongs to the tyrosine kinase receptor family ErbB/HER that comprise four members, called ErbB1-4 or HER1-4. EGFR is activated by several specific ligands broadcasting intracellular signals that depending on cellular context can promote processes or cell proliferation, differentiation, survival, migration and apoptosis. All these processes become altered during cancerigenesis and are frequently associated to oncogenic dysfunctions determined by EGFR over-expression or hyperactive mutations. Tumoral cells are literally addicted to oncogenic signals emitted from such altered EGFR, as reflected in their higher sensitivity to EGFR inhibitors than normal cells. The same is valid for other ErbB/HER family members, which are also crucial for the oncogenic action of EGFR due to the formation of heterodimers. Thus, EGFR is an important target for developing new drugs and strategies for targeted and personalized anti-tumoral therapies. Treatments can be personalized and optimized by tumor analysis of biomarkers of sensitivity. So far, the strategies has been focused on directing drugs to the EGFR molecule itself, attempting to inhibit either ligand binding with antibodies or the receptor tyrosine-kinase activity with small molecules. Drugs in clinical use include humanized monoclonal antibodies to block ligand binding (e.g. Cetuximab and Panatinumab) and drugs that compete for ATP binding to the active site of the EGFR tyrosine kinase (Gefitinib and Erlotinib), inhibiting its activity. Although clinical data support the notion that EGFR is a good target for targeted and personalized anti-tumoral treatments, the efficacy of these drugs remains limited, being usually restricted to small subgrups of sensitive patients In addition, a general problem to kinase inhibitors is the relatively frequent apparition of mutations conferring resistance to the treatment. It is necessary to have novel pharmaceutics with different and complementary mechanisms of actions from those currently in use.

Our invention proposes an innovative strategy, which is to use small drugs for pharmacological perturbation of EGFR endocytic behavior. Inducement of EGFR removal from the cell surface through endocytic internalization decreases its accessibility to extracellular activating stimuli, while altering the intracellular trafficking of activated EGFR changes the cellular location of its signal broadcasting. Both alternatives can be deleterious for tumoral cells that base their malignancy on an exaggerated EGFR signaling activity at the cell surface. Small drugs that induce EGFR endocytosis can inhibit proliferation and viability of EGFR-dependent tumoral malignant cells. This strategy (depicted in FIG. 4) is novel and innovative. It has not been used before, as it is based on experimental data obtained in our laboratory. We have demonstrated that propranolol (racemic mixtures of L and D propranolol) used as inhibitor of phosphatidic acid phosphohydrolase (PAP) activity induce endocytosis and intracellular accumulation of EGFR, independently of ligand (122). We also showed that this effect depends on a signaling pathway involving increments of phosphatidic acid (PA) that activate type 4 phosphodiesterases, leading to decreased cAMP and consequently to decreased PKA activity. Our previous studies have also shown that inhibition of PKA delays the degradation of activated EGFR by retarding its sorting to lysosomes. Because propranolol has beta-blocker activity due to its contents of L-proprapranolol enantiomer, it cannot be used in clinics at the high concentrations required to elicit PAP inhibition. In this invention we have shown that EGFR endocytosis can be also triggered by D-propranolol that lacks beta-blocker activity. Desipramine, another drug use in clinics to treat depression, has as side effect the inhibition of PAP and as such was used in this invention to increase the effect of D-propranolol. After activation of the PA/PKA signaling pathway by PAP inhibition, the EGFR is internalized and thus becomes inaccessible to external mitogenic stimuli. These observations open the possibility of using this PA/PKA signaling pathway to design new pharmaceutical formulations to counteract the malignancy of a large proportion of cancers that depend on onconic alterations of the EGFR, including overexpression and activating mutations.

The feasibility of this strategy is demonstrated by our additional results. We have observed that D-propranol (that practically lacks beta-blocker activity) and desipramine, both used as PAP inhibitors, not only induce EGFR endocytosis but also inhibit proliferation and decrease viability of tumoral cancer cells that overexpress the EGFR (glioblastoma cells GBM1 derived from a patient) or the oncogenic variant EGFRvIII (U87 cells transfected for EGFRvIII). These drugs are also effective against lung cancer cells that express the oncogenic double mutant $EGFR^{L858R/T790M}$ that is resistant to erlotinib and gefitinib. Other tumoral cells sensitive to the drugs are melanoma and ovarian cancer cells, all of which have been widely described to depend on oncogenic contribution of EGFR or other ErbB/HER family members. The combination of D-propranolol and desipramine results more effective.

The invention is extensive to cancers that express other oncogenic variants of the EGFR or other members of the ErbB/HER family (e.g. ErbB2/Neu, ErbB3/HER3 or ErbB4/HER4). It is also extensible to other compounds that have inhibitory actions upon PAP, either already known compounds (e.g. esphingosine y chlorpromazine) or any other new compound that might appear in the future. PAP inhibitors as proposed in this invention can be used to treat a variety of cancers. This includes cancers for which anti-ErbB/HER drugs have been approved for clinical treatments, such as cancers of lung, breast, head and neck and pancreas. It also include cancers where the EGFR or other ErbB/HER family members that form heterodimers with EGFR have been reported to contribute to their malignancy, even though the current anti-ErbB/HER drugs have been shown ineffective or are still under study. Cancers of ovary, stomach and esophagus, liver, prostate, as well as melanomas and glioblastoma are include in this category. The treatment proposed by the invention can complement other treatments or be unique when resistance to chemotherapies or EGFR inhibitory drugs has already developed.

SUMMARY

The present invention describes the use of compounds and combination of them that inhibit phosphatidic phosphohydrolase (PAP) enzymatic activity for the formulation of pharmaceuticals useful in cancer treatment: inhibitors of PAP are used here for blocking the progression of cancers that depend on the epidermal growth factor receptor (EGFR), its oncogenic variants and other members of its ErbB tyrosine kinase receptor family, through induction of their endocytosis and perturbation of intracellular endocytic trafficking, thus making them inaccessible to the extracellular stimuli and altering signaling that promote maintenance and progression of cancer; among PAP inhibitors that are part of the invention are D-propranolol that lacks the beta-blocker activity of L-propranolol and desipramine, both previously used for other clinical purposes; the present invention encompasses all known PAP inhibitors and all new PAP inhibitors that might appear in the future.

BIBLIOGRAFIA

1. Kok B P, Venkatraman G, Capatos D, & Brindley D N (2012) Unlike two peas in a pod: lipid phosphate phosphatases and phosphatidate phosphatases. (Translated from eng) Chem Rev 112(10):5121-5146 (in eng).
2. Yarden Y & Pines G (2012) The ERBB network: at last, cancer therapy meets systems biology. (Translated from eng) Nat Rev Cancer 12(8):553-563 (in eng).
3. Yarden Y & Sliwkowski M X (2001) Untangling the ErbB signalling network. Nat Rev Mol Cell Biol 2(2):127-137.
4. Ciardiello F & Tortora G (2008) EGFR antagonists in cancer treatment. (Translated from eng) N Engl J Med 358(11):1160-1174 (in eng).
5. Baselga J & Swain S M (2009) Novel anticancer targets: revisiting ERBB2 and discovering ERBB3. (Translated from eng) Nat Rev Cancer 9(7):463-475 (in eng).
6. Zhang H, et al. (2007) ErbB receptors: from oncogenes to targeted cancer therapies. (Translated from eng) J Clin Invest 117(8):2051-2058 (in eng).
7. Koul O & Hauser G (1987) Modulation of rat brain cytosolic phosphatidate phosphohydrolase: effect of cationic amphiphilic drugs and divalent cations. Arch Biochem Biophys 253(2):453-461.
8. Jamal Z, Martin A, Gomez-Munoz A, & Brindley D N (1991) Plasma membrane fractions from rat liver contain a phosphatidate phosphohydrolase distinct from that in the endoplasmic reticulum and cytosol. (Translated from eng) J Biol Chem 266(5):2988-2996 (in eng).
9. Grange M, Picq M, Prigent A F, Lagarde M, & Nemoz G (1998) Regulation of PDE-4 cAMP phosphodiesterases by phosphatidic acid. Cell Biochem Biophys 29(1-2):1-17.
10. Holmsen H & Dangelmaier C A (1990) Trifluoperazine enhances accumulation and inhibits phosphohydrolysis of phosphatidate in thrombin-stimulated platelets. (Translated from eng) Thromb Haemost 64(2):307-311 (in eng).
11. Alexander R W, Williams L T, & Lefkowitz R J (1975) Identification of cardiac beta-adrenergic receptors by (minus) [3H]alprenolol binding. (Translated from eng) Proc Natl Acad Sci USA 72(4):1564-1568 (in eng).
12. Howe R & Shanks R G (1966) Optical isomers of propranolol. (Translated from eng) Nature 210(5043):1336-1338 (in eng).
13. Shand D G (1975) Drug therapy: Propranolol. (Translated from eng) N Engl J Med 293(6):280-285 (in eng).
14. Murray K T, et al. (1990) Suppression of ventricular arrhythmias in man by d-propranolol independent of beta-adrenergic receptor blockade. (Translated from eng) J Clin Invest 85(3):836-842 (in eng).
15. Grange M, et al. (2000) The cAMP-specific phosphodiesterase PDE4D3 is regulated by phosphatidic acid binding. Consequences for cAMP signaling pathway and characterization of a phosphatidic acid binding site. (Translated from English) J Biol Chem 275(43):33379-33387 (in English).
16. Frazer A (2001) Serotonergic and noradrenergic reuptake inhibitors: prediction of clinical effects from in vitro potencies. (Translated from eng) J Clin Psychiatry 62 Suppl 12:16-23 (in eng).
17. Pao W & Chmielecki J (2010) Rational, biologically based treatment of EGFR-mutant non-small-cell lung cancer. (Translated from eng) Nat Rev Cancer 10(11):760-774 (in eng).
18. Gan H K, Kaye A H, & Luwor R B (2009) The EGFRvIII variant in glioblastoma multiforme. (Translated from eng) J Clin Neurosci 16(6):748-754 (in eng).
19. Nyati M K, Morgan M A, Feng F Y, & Lawrence T S (2006) Integration of EGFR inhibitors with radiochemotherapy. (Translated from eng) Nat Rev Cancer 6(11):876-885 (in eng).
20. Carlsson J (2012) Potential for clinical radionuclide-based imaging and therapy of common cancers expressing EGFR-family receptors. (Translated from eng) Tumour Biol 33(3):653-659 (in eng).
21. Cai Z, et al. (2010) Targeting erbB receptors. (Translated from eng) Semin Cell Dev Biol 21(9):961-966 (in eng).
22. Garrett J T & Arteaga C L (2011) Resistance to HER2-directed antibodies and tyrosine kinase inhibitors: mechanisms and clinical implications. (Translated from eng) Cancer Biol Ther 11(9):793-800 (in eng).
23. Saxena R & Dwivedi A (2012) ErbB family receptor inhibitors as therapeutic agents in breast cancer: current status and future clinical perspective. (Translated from eng) Med Res Rev 32(1):166-215 (in eng).
24. Custodio A & Feliu J (2013) Prognostic and predictive biomarkers for epidermal growth factor receptor-targeted therapy in colorectal cancer: beyond KRAS mutations. (Translated from eng) Crit Rev Oncol Hematol 85(1):45-81 (in eng).
25. Heinemann V, Douillard J Y, Ducreux M, & Peeters M (2013) Targeted therapy in metastatic colorectal cancer—an example of personalised medicine in action. (Translated from eng) Cancer Treat Rev 39(6):592-601 (in eng).
26. Sharafinski M E, Ferris R L, Ferrone S, & Grandis J R (2010) Epidermal growth factor receptor targeted therapy of squamous cell carcinoma of the head and neck. (Translated from eng) Head Neck 32(10):1412-1421 (in eng).
27. Mehra R, et al. (2011) Protein-intrinsic and signaling network-based sources of resistance to EGFR- and ErbB family-targeted therapies in head and neck cancer. (Translated from eng) Drug Resist Updat 14(6):260-279 (in eng).
28. Luedke E, Jaime-Ramirez A C, Bhave N, & Carson W E, 3rd (2012) Monoclonal antibody therapy of pancreatic cancer with cetuximab: potential for immune modulation. (Translated from eng) J Immunother 35(5):367-373 (in eng).
29. Yap T A, Carden C P, & Kaye S B (2009) Beyond chemotherapy: targeted therapies in ovarian cancer. (Translated from eng) Nat Rev Cancer 9(3):167-181 (in eng).
30. Paatero I, et al. (2013) CYT-1 isoform of ErbB4 is an independent prognostic factor in serous ovarian cancer and selectively promotes ovarian cancer cell growth in vitro. (Translated from eng) Gynecol Oncol 129(1):179-187 (in eng).
31. Frederick P J, Straughn J M, Jr., Alvarez R D, & Buchsbaum D J (2009) Preclinical studies and clinical utilization of monoclonal antibodies in epithelial ovarian cancer. (Translated from eng) Gynecol Oncol 113(3):384-390 (in eng).
32. Gui T & Shen K (2012) The epidermal growth factor receptor as a therapeutic target in epithelial ovarian cancer. (Translated from eng) Cancer Epidemiol 36(5):490-496 (in eng).
33. Serrano-Olvera A, Duenas-Gonzalez A, Gallardo-Rincon D, Candelaria M, & De la Garza-Salazar J (2006) Prognostic, predictive and therapeutic implications of HER2 in invasive epithelial ovarian cancer. (Translated from eng) Cancer Treat Rev 32(3):180-190 (in eng).
34. Goff B A, et al. (1996) Overexpression and relationships of HER-2/neu, epidermal growth factor receptor, p53, Ki-67, and tumor necrosis factor alpha in epithelial ovarian cancer. (Translated from eng) Eur J Gynaecol Oncol 17(6): 487-492 (in eng).
35. Pazo Cid R A & Anton A (2013) Advanced HER2-positive gastric cancer: current and future targeted therapies. (Translated from eng) Crit Rev Oncol Hematol 85(3):350-362 (in eng).

36. Luber B, et al. (2011) Biomarker analysis of cetuximab plus oxaliplatin/leucovorin/5-fluorouracil in first-line metastatic gastric and oesophago-gastric junction cancer: results from a phase II trial of the Arbeitsgemeinschaft lnternistische Onkologie (AIO). (Translated from eng) BMC Cancer 11:509 (in eng).
37. Lorenzen S & Lordick F (2011) How will human epidermal growth factor receptor 2-neu data impact clinical management of gastric cancer? (Translated from eng) Curr Opin Oncol 23(4):396-402 (in eng).
38. Maresch J, Schoppmann S F, Thallinger C M, Zielinski C C, & Hejna M (2012) Her-2/neu gene amplification and over-expression in stomach and esophageal adenocarcinoma: from pathology to treatment. (Translated from eng) Crit Rev Oncol Hematol 82(3):310-322 (in eng).
39. Chan S L & Yeo W (2012) Targeted therapy of hepatocellular carcinoma: present and future. (Translated from eng) J Gastroenterol Hepatol 27(5):862-872 (in eng).
40. Whittaker S, Marais R, & Zhu A X (2010) The role of signaling pathways in the development and treatment of hepatocellular carcinoma. (Translated from eng) Oncogene 29(36):4989-5005 (in eng).
41. Mimeault M, Johansson S L, & Batra S K (2012) Pathobiological implications of the expression of EGFR, pAkt, NF-kappaB and MIC-1 in prostate cancer stem cells and their progenies. (Translated from eng) PLoS One 7(2): e31919 (in eng).
42. Mimeault M & Batra S K (2011) Frequent gene products and molecular pathways altered in prostate cancer- and metastasis-initiating cells and their progenies and novel promising multitargeted therapies. (Translated from eng) Mol Med 17(9-10):949-964 (in eng).
43. Mimeault M & Batra S K (2012) Novel biomarkers and therapeutic targets for optimizing the therapeutic management of melanomas. (Translated from eng) World J Clin Oncol 3(3):32-42 (in eng).
44. Bracher A, et al. (2013) Epidermal growth factor facilitates melanoma lymph node metastasis by influencing tumor lymphangiogenesis. (Translated from eng) J Invest Dermatol 133(1):230-238 (in eng).
45. Gordon-Thomson C, Jones J, Mason R S, & Moore G P (2005) ErbB receptors mediate both migratory and proliferative activities in human melanocytes and melanoma cells. (Translated from eng) Melanoma Res 15(1):21-28 (in eng).
46. Abel E V, et al. (2013) Melanoma adapts to RAF/MEK inhibitors through FOXD3-mediated upregulation of ERBB3. (Translated from eng) J Clin Invest 123(5):2155-2168 (in eng).
47. Belleudi F, et al. (2012) Monoclonal antibody-induced ErbB3 receptor internalization and degradation inhibits growth and migration of human melanoma cells. (Translated from eng) Cell Cycle 11(7):1455-1467 (in eng).
48. Trinks C, Djerf E A, Hallbeck A L, Jonsson J I, & Walz T M (2010) The pan-ErbB receptor tyrosine kinase inhibitor canertinib induces ErbB-independent apoptosis in human leukemia (HL-60 and U-937) cells. (Translated from eng) Biochem Biophys Res Commun 393(1):6-10 (in eng).
49. Djerf E A, et al. (2009) ErbB receptor tyrosine kinases contribute to proliferation of malignant melanoma cells: inhibition by gefitinib (ZD1839). (Translated from eng) Melanoma Res 19(3):156-166 (in eng).
50. Djerf Severinsson E A, et al. (2011) The pan-ErbB receptor tyrosine kinase inhibitor canertinib promotes apoptosis of malignant melanoma in vitro and displays anti-tumor activity in vivo. (Translated from eng) Biochem Biophys Res Commun 414(3):563-568 (in eng).
51. Prickett T D, et al. (2009) Analysis of the tyrosine kinome in melanoma reveals recurrent mutations in ERBB4. (Translated from eng) Nat Genet 41(10):1127-1132 (in eng).
52. Del Vecchio C A, et al. (2012) EGFRvIII gene rearrangement is an early event in glioblastoma tumorigenesis and expression defines a hierarchy modulated by epigenetic mechanisms. (Translated from English) Oncogene (in English).
53. Lassman A B, Abrey L E, & Gilbert M R (2006) Response of glioblastomas to EGFR kinase inhibitors. N Engl J Med 354(5):525-526; author reply 525-526.
54. Mellinghoff I K, et al. (2005) Molecular determinants of the response of glioblastomas to EGFR kinase inhibitors. (Translated from eng) N Engl J Med 353(19):2012-2024 (in eng).
55. Hegi M E, Rajakannu P, & Weller M (2012) Epidermal growth factor receptor: a re-emerging target in glioblastoma. (Translated from eng) Curr Opin Neurol 25(6):774-779 (in eng).
56. Di Fiore P P & De Camilli P (2001) Endocytosis and signaling. an inseparable partnership. Cell 106(1):1-4.
57. Sorkin A & von Zastrow M (2009) Endocytosis and signalling: intertwining molecular networks. (Translated from eng) Nat Rev Mol Cell Biol 10(9):609-622 (in eng).
58. Brankatschk B, et al. (2012) Regulation of the EGF transcriptional response by endocytic sorting. (Translated from eng) Sci Signal 5(215):ra21 (in eng).
59. Ceresa B P & Schmid S L (2000) Regulation of signal transduction by endocytosis. Curr Opin Cell Biol 12(2): 204-210.
60. Miaczynska M, Pelkmans L, & Zerial M (2004) Not just a sink: endosomes in control of signal transduction. Curr Opin Cell Biol 16(4):400-406.
61. Mellinghoff I (2007) Why do cancer cells become "addicted" to oncogenic epidermal growth factor receptor? (Translated from eng) PLoS Med 4(10):1620-1622 (in eng).
62. Boyle D P, Mullan P, & Salto-Tellez M (2013) Molecular mapping the presence of druggable targets in preinvasive and precursor breast lesions: a comprehensive review of biomarkers related to therapeutic interventions. (Translated from eng) Biochim Biophys Acta 1835(2):230-242 (in eng).
63. Kruser T J & Wheeler D L (2010) Mechanisms of resistance to HER family targeting antibodies. (Translated from eng) Exp Cell Res 316(7):1083-1100 (in eng).
64. Buvinic S, Bravo-Zehnder M, Boyer J L, Huidobro-Toro J P, & Gonzalez A (2007) Nucleotide P2Y1 receptor regulates EGF receptor mitogenic signaling and expression in epithelial cells. (Translated from eng) J Cell Sci 120(Pt 24):4289-4301 (in eng).
65. Parkin D M & Bray F (2009) Evaluation of data quality in the cancer registry: principles and methods Part II. Completeness. (Translated from eng) Eur J Cancer 45(5):756-764 (in eng).
66. Thun M J, Delancey J O, Center M M, Jemal A, & Ward E (2009) The global burden of cancer: priorities for prevention. Carcinogenesis Epub ahead of print.
67. Parkin D M, Bray F, Ferlay J, & Pisani P (2005) Global cancer statistics, 2002. (Translated from eng) CA Cancer J Clin 55(2):74-108 (in eng).
68. Wen P Y & Kesari S (2008) Malignant gliomas in adults. (Translated from eng) N Engl J Med 359(5):492-507 (in eng).

69. Hanahan D & Weinberg R A (2011) Hallmarks of cancer: the next generation. (Translated from eng) Cell 144(5):646-674 (in eng).
70. Hanahan D & Weinberg R A (2000) The hallmarks of cancer. (Translated from eng) Cell 100(1):57-70 (in eng).
71. Vogelstein B & Kinzler K W (2004) Cancer genes and the pathways they control. (Translated from eng) Nat Med 10(8):789-799 (in eng).
72. Weinstein I B & Joe A (2008) Oncogene addiction. (Translated from eng) Cancer Res 68(9):3077-3080; discussion 3080 (in eng).
73. Klein S & Levitzki A (2009) Targeting the EGFR and the PKB pathway in cancer. (Translated from Eng) Curr Opin Cell Biol (in Eng).
74. Avraham R & Yarden Y (2011) Feedback regulation of EGFR signalling: decision making by early and delayed loops. (Translated from eng) Nat Rev Mol Cell Biol 12(2):104-117 (in eng).
75. Carpenter G (2000) The EGF receptor: a nexus for trafficking and signaling. Bioessays 22(8):697-707.
76. Gschwind A, Fischer O M, & Ullrich A (2004) The discovery of receptor tyrosine kinases: targets for cancer therapy. Nat Rev Cancer 4(5):361-370.
77. Hirsch F R, et al. (2003) Epidermal growth factor receptor in non-small-cell lung carcinomas: correlation between gene copy number and protein expression and impact on prognosis. (Translated from eng) J Clin Oncol 21(20):3798-3807 (in eng).
78. Wong A J, et al. (1987) Increased expression of the epidermal growth factor receptor gene in malignant gliomas is invariably associated with gene amplification. (Translated from eng) Proc Natl Acad Sci USA 84(19):6899-6903 (in eng).
79. Dragovich T & Campen C (2009) Anti-EGFR-Targeted Therapy for Esophageal and Gastric Cancers: An Evolving Concept. (Translated from eng) J Oncol 2009: 804108 (in eng).
80. Wagner A D & Moehler M (2009) Development of targeted therapies in advanced gastric cancer: promising exploratory steps in a new era. (Translated from eng) Curr Opin Oncol 21(4):381-385 (in eng).
81. Pelloski C E, et al. (2007) Epidermal growth factor receptor variant III status defines clinically distinct subtypes of glioblastoma. (Translated from eng) J Clin Oncol 25(16):2288-2294 (in eng).
82. Irmer D, Funk J O, & Blaukat A (2007) EGFR kinase domain mutations—functional impact and relevance for lung cancer therapy. (Translated from eng) Oncogene 26(39):5693-5701 (in eng).
83. Sharma S V, Bell D W, Settleman J, & Haber D A (2007) Epidermal growth factor receptor mutations in lung cancer. (Translated from eng) Nat Rev Cancer 7(3):169-181 (in eng).
84. Gazdar A F, Shigematsu H, Herz J, & Minna J D (2004) Mutations and addiction to EGFR: the Achilles 'heal' of lung cancers? (Translated from eng) Trends Mol Med 10(10):481-486 (in eng).
85. Jonker D J, et al. (2007) Cetuximab for the treatment of colorectal cancer. (Translated from eng) N Engl J Med 357(20):2040-2048 (in eng).
86. Van Cutsem E, et al. (2009) Cetuximab and chemotherapy as initial treatment for metastatic colorectal cancer. (Translated from eng) N Engl J Med 360(14):1408-1417 (in eng).
87. Klein S & Levitzki A (2007) Targeted cancer therapy: promise and reality. (Translated from eng) Adv Cancer Res 97:295-319 (in eng).
88. Rosell R, et al. (2009) Screening for epidermal growth factor receptor mutations in lung cancer. (Translated from eng) N Engl J Med 361(10):958-967 (in eng).
89. Rosell R, et al. (2009) Customized treatment in non-small-cell lung cancer based on EGFR mutations and BRCA1 mRNA expression. (Translated from eng) PLoS One 4(5):e5133 (in eng).
90. Zhang X, et al. (2008) Mutations of epidermal growth factor receptor in colon cancer indicate susceptibility or resistance to gefitinib. (Translated from eng) Oncol Rep 19(6):1541-1544 (in eng).
91. Chan S K, Gullick W J, & Hill M E (2006) Mutations of the epidermal growth factor receptor in non-small cell lung cancer—search and destroy. Eur J Cancer 42(1):17-23.
92. Bezjak A, et al. (2006) Symptom improvement in lung cancer patients treated with erlotinib: quality of life analysis of the National Cancer Institute of Canada Clinical Trials Group Study BR.21. (Translated from eng) J Clin Oncol 24(24):3831-3837 (in eng).
93. Belani C P, et al. (2008) Cetuximab in combination with carboplatin and docetaxel for patients with metastatic or advanced-stage nonsmall cell lung cancer: a multicenter phase 2 study. (Translated from eng) Cancer 113(9):2512-2517 (in eng).
94. Paez J G, et al. (2004) EGFR mutations in lung cancer: correlation with clinical response to gefitinib therapy. (Translated from eng) Science 304(5676):1497-1500 (in eng).
95. Lynch T J, et al. (2004) Activating mutations in the epidermal growth factor receptor underlying responsiveness of non-small-cell lung cancer to gefitinib. (Translated from eng) N Engl J Med 350(21):2129-2139 (in eng).
96. Sequist L V, et al. (2008) First-line gefitinib in patients with advanced non-small-cell lung cancer harboring somatic EGFR mutations. (Translated from eng) J Clin Oncol 26(15):2442-2449 (in eng).
97. Costa D B, Kobayashi S, Tenen D G, & Huberman M S (2007) Pooled analysis of the prospective trials of gefitinib monotherapy for EGFR-mutant non-small cell lung cancers. (Translated from eng) Lung Cancer 58(1):95-103 (in eng).
98. Tamura K, et al. (2008) Multicentre prospective phase II trial of gefitinib for advanced non-small cell lung cancer with epidermal growth factor receptor mutations: results of the West Japan Thoracic Oncology Group trial (WJ-TOG0403). (Translated from eng) Br J Cancer 98(5):907-914 (in eng).
99. Zhou W, et al. (2009) Novel mutant-selective EGFR kinase inhibitors against EGFR T790M. (Translated from eng) Nature 462(7276):1070-1074 (in eng).
100. Knight Z A, Lin H, & Shokat K M (2010) Targeting the cancer kinome through polypharmacology. (Translated from eng) Nat Rev Cancer 10(2):130-137 (in eng).
101. Pao W, et al. (2005) Acquired resistance of lung adenocarcinomas to gefitinib or erlotinib is associated with a second mutation in the EGFR kinase domain. (Translated from eng) PLoS Med 2(3):e73 (in eng).
102. Ogino A, et al. (2007) Emergence of epidermal growth factor receptor T790M mutation during chronic exposure to gefitinib in a non small cell lung cancer cell line. (Translated from eng) Cancer Res 67(16):7807-7814 (in eng).
103. Yun C H, et al. (2008) The T790M mutation in EGFR kinase causes drug resistance by increasing the affinity for ATP. (Translated from eng) Proc Natl Acad Sci USA 105(6):2070-2075 (in eng).
104. Rush J S, Quinalty L M, Engelman L, Sherry D M, & Ceresa B P (2012) Endosomal accumulation of the acti- 105. Hyatt D C & Ceresa B P (2008) Cellular localization of the activated EGFR determines its effect on cell growth in MDA-MB-468 cells. (Translated from eng) Exp Cell Res 314(18):3415-3425 (in eng).

106. Roepstorff K, Grøvdal L, Grandal M, Lerdrup M, & Van Deurs B (2008) Endocytic downregulation of ErbB receptors: mechanisms and relevance in cancer. Histochem Cell Biol 129(5):563-578.

107. Miaczynska M, et al. (2004) APPL proteins link Rab5 to nuclear signal transduction via an endosomal compartment. Cell 116(3):445-456.

108. Wells A, et al. (1990) Ligand-induced transformation by a noninternalizing epidermal growth factor receptor. Science 247(4945):962-964.

109. Vieira A V, Lamaze C, & Schmid S L (1996) Control of EGF receptor signaling by clathrin-mediated endocytosis. Science 274(5295):2086-2089.

110. Mosesson Y, Mills G B, & Yarden Y (2008) Derailed endocytosis: an emerging feature of cancer. (Translated from eng) Nat Rev Cancer 8(11):835-850 (in eng).

111. Bache K G, Slagsvold T, & Stenmark H (2004) Defective downregulation of receptor tyrosine kinases in cancer. Embo J 23(14):2707-2712.

112. Schlessinger J (2002) Ligand-induced, receptor-mediated dimerization and activation of EGF receptor. Cell 110(6):669-672.

113. de Melker A A, van der Horst G, Calafat J, Jansen H, & Borst J (2001) c-Cbl ubiquitinates the EGF receptor at the plasma membrane and remains receptor associated throughout the endocytic route. (Translated from eng) J Cell Sci 114(Pt 11):2167-2178 (in eng).

114. Stang E, et al. (2004) Cbl-dependent ubiquitination is required for progression of EGF receptors into clathrin-coated pits. Mol Biol Cell 15(8):3591-3604.

115. Thien C B, Walker F, & Langdon W Y (2001) RING finger mutations that abolish c-Cbl-directed polyubiquitination and downregulation of the EGF receptor are insufficient for cell transformation. Mol Cell 7(2):355-365.

116. Goh L K, Huang F, Kim W, Gygi S, & Sorkin A (2010) Multiple mechanisms collectively regulate clathrin-mediated endocytosis of the epidermal growth factor receptor. (Translated from eng) J Cell Biol 189(5):871-883 (in eng).

117. Eden E R, Huang F, Sorkin A, & Futter C E (2012) The role of EGF receptor ubiquitination in regulating its intracellular traffic. (Translated from eng) Traffic 13(2):329-337 (in eng).

118. Levkowitz G, et al. (1999) Ubiquitin ligase activity and tyrosine phosphorylation underlie suppression of growth factor signaling by c-Cbl/Sli-1. Mol Cell 4(6):1029-1040.

119. Katzmann D J, Odorizzi G, & Emr S D (2002) Receptor downregulation and multivesicular-body sorting. Nat Rev Mol Cell Biol 3(12):893-905.

120. Wegner C S, Rodahl L M, & Stenmark H (2011) ESCRT proteins and cell signalling. (Translated from eng) Traffic 12(10):1291-1297 (in eng).

121. Sigismund S, et al. (2008) Clathrin-mediated internalization is essential for sustained EGFR signaling but dispensable for degradation. (Translated from eng) Dev Cell 15(2):209-219 (in eng).

122. Norambuena A, et al. (2010) Phosphatidic Acid Induces Ligand-independent Epidermal Growth Factor Receptor Endocytic Traffic through PDE4 Activation. Mol Biol Cell 21(16):2916-2929.

123. Wang X, Devaiah S P, Zhang W, & Welti R (2006) Signaling functions of phosphatidic acid. Prog Lipid Res 45(3):250-278.

124. Jenkins G M & Frohman M A (2005) Phospholipase D: a lipid centric review. Cell Mol Life Sci 62(19-20):2305-2316.

125. McDermott M, Wakelam M J, & Morris A J (2004) Phospholipase D. Biochem Cell Biol 82(1):225-253.

126. Foster D A & Xu L (2003) Phospholipase D in cell proliferation and cancer. Mol Cancer Res 1(11):789-800.

127. Hornia A, et al. (1999) Antagonistic effects of protein kinase C alpha and delta on both transformation and phospholipase D activity mediated by the epidermal growth factor receptor. Mol Cell Biol 19(11):7672-7680.

128. Lu Z, et al. (2000) Phospholipase D and RalA cooperate with the epidermal growth factor receptor to transform 3Y1 rat fibroblasts. Mol Cell Biol 20(2):462-467.

129. Song J, Jiang Y W, & Foster D A (1994) Epidermal growth factor induces the production of biologically distinguishable diglyceride species from phosphatidylinositol and phosphatidylcholine via the independent activation of type C and type D phospholipases. Cell Growth Differ 5(1):79-85.

130. Foster D A (2009) Phosphatidic acid signaling to mTOR: signals for the survival of human cancer cells. (Translated from eng) Biochim Biophys Acta 1791(9):949-955 (in eng).

131. Klionsky D J (2007) Autophagy: from phenomenology to molecular understanding in less than a decade. (Translated from eng) Nat Rev Mol Cell Biol 8(11):931-937 (in eng).

132. Hecht S S, Kassie F, & Hatsukami D K (2009) Chemoprevention of lung carcinogenesis in addicted smokers and ex-smokers. (Translated from eng) Nat Rev Cancer 9(7): 476-488 (in eng).

133. Jha P (2009) Avoidable global cancer deaths and total deaths from smoking. (Translated from eng) Nat Rev Cancer 9(9):655-664 (in eng).

134. Schiller J H, et al. (2002) Comparison of four chemotherapy regimens for advanced non-small-cell lung cancer. (Translated from eng) N Engl J Med 346(2):92-98 (in eng).

135. Hohenberger P & Gretschel S (2003) Gastric cancer. (Translated from eng) Lancet 362(9380):305-315 (in eng).

136. Jemal A, et al. (2009) Cancer statistics, 2009. (Translated from eng) CA Cancer J Clin 59(4):225-249 (in eng).

137. Garrido M, et al. (2007) [Treatment of advanced gastric cancer with oxaliplatin plus 5-fluorouracil/leucovorin (FOLFOX-4 chemotherapy)]. (Translated from spa) Rev Med Chil 135(11):1380-1387 (in spa).

138. Bondy M L, et al. (2008) Brain tumor epidemiology: consensus from the Brain Tumor Epidemiology Consortium. (Translated from eng) Cancer 113(7 Suppl):1953-1968 (in eng).

139. Schwartzbaum J A, Fisher J L, Aldape K D, & Wrensch M (2006) Epidemiology and molecular pathology of glioma. (Translated from eng) Nat Clin Pract Neurol 2(9): 494-503; quiz 491 p following 516 (in eng).

140. Stupp R, et al. (2005) Radiotherapy plus concomitant and adjuvant temozolomide for glioblastoma. (Translated from eng) N Engl J Med 352(10):987-996 (in eng).

141. Stupp R, et al. (2009) Effects of radiotherapy with concomitant and adjuvant temozolomide versus radiotherapy alone on survival in glioblastoma in a randomised phase III study: 5-year analysis of the EORTC-NCIC trial. (Translated from Eng) Lancet Oncol (in Eng).

142. Barron T I, Connolly R M, Sharp L, Bennett K, & Visvanathan K (Beta blockers and breast cancer mortality:

143. Thaker P H, et al. (2006) Chronic stress promotes tumor growth and angiogenesis in a mouse model of ovarian carcinoma. (Translated from eng) Nat Med 12(8):939-944 (in eng).
144. Palm D, et al. (2006) The norepinephrine-driven metastasis development of PC-3 human prostate cancer cells in BALB/c nude mice is inhibited by beta-blockers. (Translated from eng) Int J Cancer 118(11):2744-2749 (in eng).
145. Arimochi H & Morita K (2006) Characterization of cytotoxic actions of tricyclic antidepressants on human HT29 colon carcinoma cells. (Translated from eng) Eur J Pharmacol 541(1-2):17-23 (in eng).
146. Huang C J, et al. (2007) Desipramine-induced Ca2+ movement and cytotoxicity in PC3 human prostate cancer cells. (Translated from eng) Toxicol In Vitro 21(3):449-456 (in eng).
147. Lu T, et al. (2009) Desipramine-induced Ca-independent apoptosis in Mg63 human osteosarcoma cells: dependence on P38 mitogen-activated protein kinase-regulated activation of caspase 3. (Translated from eng) Clin Exp Pharmacol Physiol 36(3):297-303 (in eng).
148. Ma J, et al. (2013) Antidepressant desipramine leads to C6 glioma cell autophagy: implication for the adjuvant therapy of cancer. (Translated from eng) Anticancer Agents Med Chem 13(2):254-260 (in eng).
149. Ma J, et al. (2011) Desipramine induces apoptosis in rat glioma cells via endoplasmic reticulum stress-dependent CHOP pathway. (Translated from eng) J Neurooncol 101(1):41-48 (in eng).
150. Hursting M J, Clark G D, Raisys V A, Miller S J, & Opheim K E (1992) Measurement of free desipramine in serum by ultrafiltration with immunoassay. (Translated from eng) Clin Chem 38(12):2468-2471 (in eng).
151. Bailey D N & Jatlow P I (1976) Gas-chromatographic analysis for therapeutic concentration of imipramine and disipramine in plasma, with use of a nitrogen detector. (Translated from eng) Clin Chem 22(10):1697-1701 (in eng).
152. Salazar G & Gonzalez A (2002) Novel mechanism for regulation of epidermal growth factor receptor endocytosis revealed by protein kinase A inhibition. (Translated from English) Mol Biol Cell 13(5):1677-1693 (in English).
153. Perry D K, Hand W L, Edmondson D E, & Lambeth J D (1992) Role of phospholipase D-derived diradylglycerol in the activation of the human neutrophil respiratory burst oxidase. Inhibition by phosphatidic acid phosphohydrolase inhibitors. J Immunol 149(8):2749-2758.
154. Ueno Y, et al. (2008) Heregulin-induced activation of ErbB3 by EGFR tyrosine kinase activity promotes tumor growth and metastasis in melanoma cells. (Translated from eng) Int J Cancer 123(2):340-347 (in eng).
155. Qiu K M, et al. (2012) Design, synthesis and biological evaluation of pyrazolyl-thiazolinone derivatives as potential EGFR and HER-2 kinase inhibitors. (Translated from eng) Bioorg Med Chem 20(6):2010-2018 (in eng).
156. Luo Y, et al. (2011) Metronidazole acid acyl sulfonamide: a novel class of anticancer agents and potential EGFR tyrosine kinase inhibitors. (Translated from eng) Bioorg Med Chem 19(20):6069-6076 (in eng).
157. Pao W & Miller V A (2005) Epidermal growth factor receptor mutations, small-molecule kinase inhibitors, and non-small-cell lung cancer: current knowledge and future directions. (Translated from eng) J Clin Oncol 23(11): 2556-2568 (in eng).
158. Fuchtner C, et al. (1993) Characterization of a human ovarian carcinoma cell line: UCI 101. (Translated from eng) Gynecol Oncol 48(2):203-209 (in eng).
159. Cancino J, et al. (2007) Antibody to AP1B adaptor blocks biosynthetic and recycling routes of basolateral proteins at recycling endosomes. (Translated from eng) Mol Biol Cell 18(12):4872-4884 (in eng).
160. Faundez V, Krauss R, Holuigue L, Garrido J, & Gonzalez A (1992) Epidermal growth factor receptor in synaptic fractions of the rat central nervous system. J Biol Chem 267(28):20363-20370.

What is claimed is:

1. A method of treating cancer in a subject in need of treatment for the cancer, comprising administering an effective amount of an inhibitor of the enzyme phosphatidic acid phosphohydrolase (PAP) to the subject in need of treatment for the cancer,
   wherein the cancer comprises tumoral cells that express epidermal growth factor receptor (EGFR), or an oncogenic variant of EGFR, or another member of the ErbB/HER family, or a combination thereof, at levels higher than the corresponding expression levels in non-tumoral cells of the same type,
   and wherein the inhibitor of PAP consists of a drug selected from the group consisting of D (+) propranolol, and a combination of D (+) propranolol with desipramine, such that the inhibitor of PAP lacks beta-blocker activity.

2. The method according to claim 1, wherein the drug is a combination of D (+) propranolol with desipramine.

3. The method according to claim 1, wherein the cancer is selected from the group consisting of lung, breast, colorectal, head and neck, pancreas, ovarian, stomach and esophagus, hepatic, prostate, melanoma and glioblastoma cancers.

4. The method according to claim 1, further comprising administering additional drugs that inhibit the epidermal growth factor receptor (EGFR), or an oncogenic variant of EGFR, or another member of the ErbB/HER family, or a combination thereof, through a pathway different from inhibition of PAP.

5. The method according to claim 1, further comprising administering a non-pharmaceutical procedure to the subject.

6. The method according to claim 5, wherein the non-pharmaceutical procedure is selected from the group consisting of radiotherapy and surgery.

* * * * *